United States Patent
Sahlberg et al.

(10) Patent No.: US 7,148,243 B2
(45) Date of Patent: Dec. 12, 2006

(54) ANTIVIRALS

(75) Inventors: Christer Sahlberg, Hagersten (SE); Rolf Noreen, Tullinge (SE); Marita Hogberg, Tulling (SE); Per Engelhardt, Stockholm (SE)

(73) Assignee: Medivir AB, Huddinge (SE)

( * ) Notice: Subject to any disclaimer, the term of this patent is extended or adjusted under 35 U.S.C. 154(b) by 320 days.

(21) Appl. No.: 10/243,118

(22) Filed: Sep. 12, 2002

(65) Prior Publication Data
US 2003/0119881 A1 Jun. 26, 2003

Related U.S. Application Data

(62) Division of application No. 09/600,309, filed as application No. PCT/SE99/00053 on Jan. 15, 1999, now Pat. No. 6,486,183.

(30) Foreign Application Priority Data

Jan. 16, 1998 (SE) .................... 9800113
Jan. 16, 1998 (SE) .................... 9800116

(51) Int. Cl.
*A61K 31/44* (2006.01)
*C07D 213/84* (2006.01)

(52) U.S. Cl. .................... 514/344; 546/286; 546/309; 514/344; 514/352

(58) Field of Classification Search ......... 514/344, 514/345, 314, 352; 546/167, 262, 289, 306, 546/286, 309
See application file for complete search history.

(56) References Cited

U.S. PATENT DOCUMENTS 5,849,769 A * 12/1998 Lind et al. ............ 514/352
6,486,183 B1 * 11/2002 Salhberg et al. .......... 514/344

OTHER PUBLICATIONS

Silverman, Richard B., "Chapter 8: Prodrugs and Drug Delivery Systems" from "The Organic Chemistry of Drug Design and Drug Action," Academic Press, Inc., pp. 352-358.*
Naesens, Lieve et al. "Antiretroviral Efficacy and Pharmacokinetics of Oral Bis(isopropyloxycarbonzyloxymethyl)-9-(2-Phosphonylmethoxypropy!)adenine in Mice," Antimicrobial Agents and Chemotherapy, Jul. 1998, vol. 42(7), pp. 1568-1573.*
Optimization of Antiviral and Kinetic Prop ICAR Sante Fe 1995 23-28/04/1995 Overview.
Synthesis and HIV-1 activities of Urea-PETT analogues, belonging to a New Series of Potent Non-Nucleoside HIV-1 Reverse Transcriptase Inhibitors Poster XIV Int.Symp Med Chem Maastricht Sep. 8-12, 1996.
The Merck Manual, Fifteenth Edition, pp. 2437-2438, Published By Merck & Co., Inc. 1987.

* cited by examiner

*Primary Examiner*—Kamal A. Saeed
*Assistant Examiner*—Janet L. Coppins
(74) *Attorney, Agent, or Firm*—Birch, Stewart, Kolasch & Birch, LLP

(57) ABSTRACT

Compounds of the formula I:

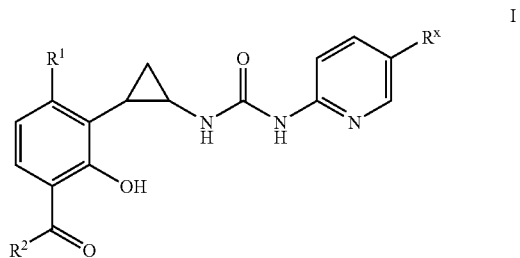

wherein
$R^x$ is cyano or bromo;
$R^1$ is halo;
$R^2$ is $C_1$ 14 $C_3$ alkyl,
and pharmaceutically acceptable salts and prodrugs thereof have activity as antiretrovirals.

6 Claims, 3 Drawing Sheets

ANTIVIRALS

This application is a divisional of application Ser. No. 09/600,309, filed on Nov. 13, 2000 now U.S. Pat. No. 6,486,183 and for which priority is claimed under 35 U.S.C. § 120. Application Ser. No. 09/600,309 is the national phase of PCT International Application No. PCT/SE99/00053 filed on Jan. 15, 1999 under 35 U.S.C. § 371. The entire contents of each of the above-identified applications are hereby incorporated by reference. This application also claims priority of Application No. SE 9800116-7 and SE 9800113-4 both filed in SWEDEN on Jan. 16, 1998 under 35 U.S.C. §119.

TECHNICAL FIELD

This invention relates to the field of antivirals and in particular to HIV reverse transcriptase inhibitors. The invention provides novel compounds, pharmaceutical compositions comprising these compounds and methods for the inhibition of HIV employing them.

BACKGROUND TO THE INVENTION

Of the pharmaceuticals which have shown clinically relevant activity in the inhibition of HIV reverse transcriptase in HIV treatment, most are nucleoside analogues such as AZT, ddI, ddC and D4T. These nucleoside analogues are not as specific as is desirable and thus have to be administered at relatively high dosage levels. At these dosage levels, nucleoside analogues tend to be rather toxic, limiting their long term use.

To overcome these problems of specificity and toxicity a number of non-nucleoside inhibitors of the reverse transcriptase of HIV have been developed. For example TIBO, a reverse transcriptase from Janssen inhibits HIV at nanomolar concentrations and displays no clinically significant toxicity. Both TIBO and the non nucleotide reverse transcriptase inhibitor nevirapine proceeded rapidly to phase II clinical trials in patients. However it soon became apparent that these non-nucleoside inhibitors rapidly select out HIV mutants in vivo which are resistant to the usual dosages of the respective inhibitors. In the case of nevirapine for example, after only four weeks of therapy virus isolated from patient serum was 100 fold less sensitive to the drug compared with virus isolated from untreated patients (Drug Design & Discovery 1992 8 pp 255–263). A similar pattern has emerged for other non-nucleoside RT inhibitors which have entered clinical trials, L-697661 (Merck) and delavirdine (U-87201 (Upjohn)), namely that promising in vitro activity has rapidly produced resistant HIV mutants when adminstered to patients. Notwithstanding this drawback nevirapine and delavirdine have recently been registered for clinical use, although limited to specific coadministration regimes in an attempt to retard resistance development.

International patent application no WO 95/06034 describes a series of novel urea derivatives which exhibit good in vitro activity against HIV reverse transcriptase and good inhibition of HIV replication in cell culture. However practical deployment of the compounds in WO 95/06034 is hampered by their poor pharmacokinetic performance. Additionally, as with many non-nucleoside reverse transcriptase inhibitors, the compounds presented in WO 95/06034 leave room for improvement in the key parameter of slow resistance development and a favourable pattern of activiy against HIV mutants generated by other antiviral regimes.

A poster of Öberg et al at the 1995 ICAR at Santa Fe disclosed inter alia a racemic compound nominally within the abovementioned WO 95/06034 and having the formula:

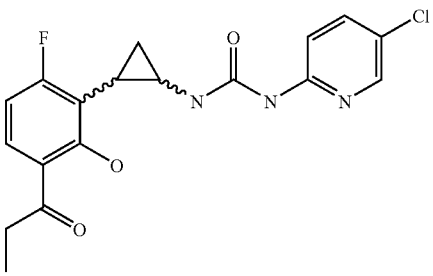

At the time the above depicted compound was regarded as of less interest than thiourea variants having a methoxy/acetyl bearing phenyl ring. However, we have now discovered that an alternative substitution pattern manifests an improved resistance pattern in comparison to these prior art compounds in conjunction with good pharmacokinetic performance and a prolonged time to virus resistance. The invention thus provides inhibitors which combine the superior specificity of non-nucleoside inhibitors with the clinical practicality missing from all prior art inhibitors.

BRIEF DESCRIPTIONS OF THE INVENTION

In accordance with the invention there are provided compounds of the formula I

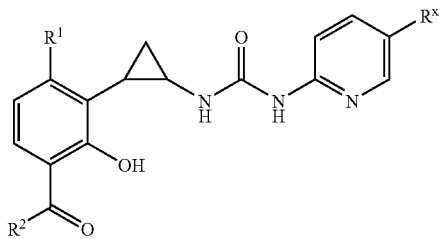

wherein
$R^1$ is halo;
$R^2$ is $C_1$–$C_3$ alkyl;
$R^x$ is cyano or bromo;

and pharmaceutically acceptable salts and prodrugs thereof.

The invention further provides pharmaceutical compositions comprising the compounds of formula I and pharmaceutically acceptable carriers or diluents therefor. Additional aspects of the invention provide methods for the inhibition of HIV comprising administering a compound of the formula I to a subject afflicted with HIV. The invention also extends to the use of the compounds of formula I in therapy, such as in the preparation of a medicament for the treatment of HIV infections.

In treating conditions caused by HIV, the compounds of formula I are preferably administered in an amount to achieve a plasma level of around 10 to 1000 nM and more preferably 100 to 500 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500–750 mg, in one to four dosage units per day.

A preferred subset of compounds within claim 1, particularly with regard to pharmacokinetics, has the structure IA:

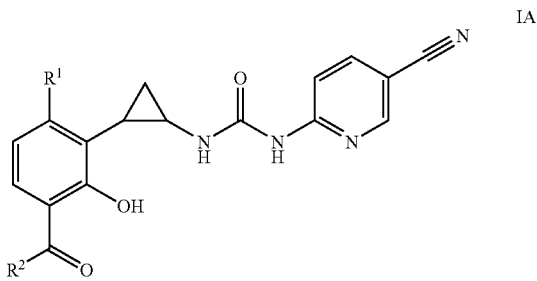

where $R^1$ and $R^2$ are as defined above, including the pharmaceutically acceptable salts and prodrugs thereof.

A further favoured subset of compounds within Formula I, particularly with regard to ease of forming prodrugs, comprise compounds wherein $R^x$ is bromo.

Preferably $R^1$ is chloro and more preferably fluoro. Suitable $R^2$ groups include methyl, isopropyl, n-propyl and preferably ethyl.

As depicted above, the cyclopropyl ring is in the cis configuration, allowing two enantiomers, 1S, 2S and 1R, 2R (respectively and non-conventionally denoted 2R, 1S and 2S,1R in SE 980016-7 and SE 9800113-4):

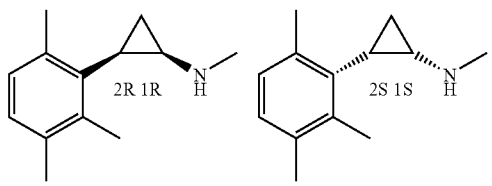

Each of these enantiomers are potent antiretrovirals, although the different enantiomers can display subtle differences in physiological properties. For instance the 1S, 2S and 1R,2R enantiomers can show a different pattern of metabolism within the P450 system. The 1S,2S enantiomer of compounds wherein $R^x$ is cyano is particularly preferred as it appears unique in being able to avoid key components of the P450 system. Other retroviral agents such as the HIV protease inhibitor ritonavir interact extensively with the P450 system, leading to an array of undesirable physiological responses including extensive alteration of the metabolism of other co-administered drugs. This is of particular concern with pharmaceuticals administered for a chronic infection where patients can expect to take a number of pharmaceuticals for years, if not decades.

Suitable prodrugs of the compounds of formula I include those of the formula II:

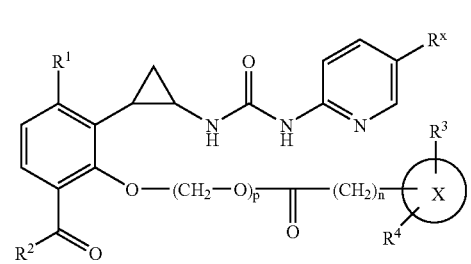

wherein
$R^1$, $R^2$ and $R^x$ are as defined above,
$R^3$ is H, $(CH_m)_n NR^5 R^6$;

$R^4$ is H, $C_1C_3$ alkyl, $(CH_m)_n NR^5 R^6$, $(CH_m)_n C(=O)R^5$, $(CH_m)$ CN; or $R^3$ and $R^4$ together define a 5 or 6 membered fused ring having 0–2 hetero atoms and/or 0–2 unsaturated bonds and/or 0–2 substituents;

$R^5$ is H, $C_1$–$C_3$ alkyl, $C(=O)R^7$ or a peptide of 1 to 4 amino acids;

$R^6$ is H, $C_1$–$C_3$ alkyl; or $R^5$ and $R^6$ together define a 5 or 6 membered ring having 0 or 1 additional hetero atom and/or 0–2 unsaturated bonds and/or 0–2 substituents;

$R^7$ is H, $C_1$–$C_{12}$ alkyl, $(CH_m)_n NR^5 R^6$;

X and its encompassing circle define a 5 or 6 membered ring having 0 to 3 unsaturated bonds and/or 0 to 3 hetero atoms selected from S, O and N;

m is independently 1 or 2;

n is independently 0, 1 or 2;

and pharmaceutically acceptable salts thereof.

Corresponding pro drugs of compounds wherein $R^x$ is chloro form a further aspect of the invention.

The ring structure containing X, hereafter referred to the X-ring, may be saturated or have 1–3 unsaturated bonds, including rings with an aromatic character. Preferred X-rings include a cyclohexanyl or cyclohexenyl ring or more preferably a phenyl ring. Other preferred X-rings include morpholino or more preferably a pyridyl ring. Alternatively, X-ring may define a five membered ring such as pentenyl or pyrrolyl.

Suitable fused ring systems for the X-ring in the event that $R^3$ and $R^4$ join to form an optionally hetero-containing ring include napthyl, quinolyl, tetrahydroisoquinolyl, indolyl or benzimidazole ring systems. Suitable substituent rings for the X-ring in the event that $R^4$ and $R^5$ join to form a ring include morpholino and piperidino. These fused or substituent rings may be may be optionally substituted with halo, halomethyl, amino such as $(CH_m)_n NR^5 R^6$, $C(=O)NR^5 R^6$, hydroxy, hydroxymethyl, carboxy, carboxymethyl, $C_{1-3}$ alkyl, $C_{1-3}$ alkoxy and the like.

The X-ring may be spaced from the adjacent carbonyl moiety by a methylene or ethylene group which may be optionally substituted with substituents such as halo, halomethyl, amino, amino methyl, hydroxy, hydroxymethyl, carboxy, carboxymethyl, $C_{1-3}$ alkyl, $C_{1-3}$ alkoxy and the like. It is preferred that the X-ring is adjacent the carbonyl.

Preferably the moiety represented by the X-ring system, $R^3$, $R^4$ and, if present $R^5$–$R^7$ has a somewhat basic character. This can be achieved by selecting a suitably basic heterocycle as the X-ring, such as pyridyl or benzopyridyl. Alternatively or additionally, one or more of $R^3$ to $R^7$ may comprise a basic substituent such as a primary, secondary or tertiary amine, an amino acid etc.

Favoured $R^3$ and/or $R^4$ groups include $NH_2$, $N(CH_2)_2$ and $NHC_1$–$C_3$ alkyl, such as $NHCH_3$ or $NHCH_2CH_3$. Preferably $R^3$ is in the meta position relative to the carbonyl and its optional spacer, especially where the X-contaning ring is phenyl or $R^3$ is in the para position when the X-containing ring is heteroaromatic, such as pyrid-3-yl. The currently preferred value for p and/or n is zero, that is the respective groups are absent.

Preferred compounds of the invention include:

(1S, 2S)-N-[cis-2-(6-fluoro, 2-hydroxy, 3-propionylphenyl)-cyclopropyl]-N'-(5-cyanopyrid-2-yl)-urea, (1S, 2S)-N-[cis-2-(6-fluoro, 2-hydroxy, 3-butyrylphenyl)-cyclopropyl]-N'-(5-cyanopyrid-2-yl)-urea, (1S, 2S)-N-[cis-2-(6-fluoro, 2-hydroxy, 3-acetylphenyl)-cyclopropyl]-N'-(5-cyanopyrid-2-yl)-urea, (1S, 2S)-N-[cis-2-(2-(3-aminophenylcarbonyloxy)-6-fluoro-3-propionylphenyl)-cyclopropyl]-N'-(5-cyanopyrid-2-yl)-urea;

(1S, 2S)-N-[cis-2-(2-(3-aminophenylcarbonyloxy)-6-fluoro-3-butyrylphenyl)-cyclopropyl]-N'-(5-cyanopyrid-2-yl)-urea;

(1S, 2S)-N-[cis-2-(2-(3-aminophenylcarbonyloxy)-6-fluoro-3-acetylphenyl)-cyclopropyl]-N'-(5-cyanopyrid-2-yl)-urea;

(1S, 2S)-N-[cis-2-(2-(3-ethylaminophenylcarbonyloxy)-6-fluoro-3-propionylphenyl)-cyclopropyl]-N'-(5-cyanopyrid-2-yl)-urea;

(1S, 2S)-N-[cis-2-(2-(3-ethylaminophenylcarbonyloxy)-6-fluoro-3-butyrylphenyl)-cyclopropyl]-N'-(5-cyanopyrid-2-yl)-urea;

(1S, 2S)-N-[cis-2-(2-(3-ethylaminophenylcarbonyloxy)-6-fluoro-3-acetylphenyl)-cyclopropyl]-N'-(5-cyanopyrid-2-yl)-urea;

(1S, 2S)-N-[cis-2-(2-(3-dimethylaminophenylcarbonyloxy)-6-fluoro-3-propionylphenyl)-cyclopropyl]-N'-(5-cyanopyrid-2-yl)-urea;

(1S, 2S)-N-[cis-2-(2-(3-dimethylaminophenylcarbonyloxy)-6-fluoro-3-butyrylphenyl)-cyclopropyl]-N'-(5-cyanopyrid-2-yl)-urea;

(1S, 2S)-N-[cis-2-(2-(3-dimethylaminophenylcarbonyloxy)-6-fluoro-3-acetylphenyl)-cyclopropyl]-N'-(5-cyanopyrid-2-yl)-urea;

and pharmaceutically acceptable salts thereof.

Other preferred compounds include (1S, 2S)-N-[cis-2-(2-(6-methylaminopyrid-3-ylcarbonyloxy)-6-fluoro-3-propionylphenyl)-cyclopropyl]-N'-(5-cyanopyrid-2-yl)-urea;

(1S, 2S)-N-[cis-2-(2-(6-methylaminopyrid-3-ylcarbonyloxy)-6-fluoro-3-butyrylphenyl)-cyclopropyl]-N'-(5-cyanopyrid-2-yl)-urea;

(1S, 2S)-N-[cis-2-(2-(6-methylaminopyrid-3-ylcarbonyloxy)-6-fluoro-3-acetylphenyl)-cyclopropyl]-N'-(5-cyanopyrid-2-yl)-urea;

(1S, 2S)-N-[cis-2-(2-(6-aminopyrid-3-ylcarbonyloxy)-6-fluoro-3-propionylphenyl)-cyclopropyl]-N'-(5-cyanopyrid-2-yl)-urea;

(1S, 2S)-N-[cis-2-(2-(6-aminopyrid-3-ylcarbonyloxy)-6-fluoro-3-butyrylphenyl)-cyclopropyl]-N'-(5-cyanopyrid-2-yl)-urea;

(1S, 2S)-N-[cis-2-(2-(6-aminopyrid-3-ylcarbonyloxy)-6-fluoro-3-acetylphenyl)-cyclopropyl]-N'-(5-cyanopyrid-2-yl)-urea;

and pharmaceutically acceptable salts thereof

Other convenient compounds of the invention include:

(1R, 2R)-N-[cis-2-(6-fluoro, 2-hydroxy, 3-propionylphenyl)-cyclopropyl]-N'-(5-cyanopyrid-2-yl)-urea, (1R, 2R)-N-[cis-2-(6-fluoro, 2-hydroxy, 3-butyrylphenyl)-cyclopropyl]-N'-(5-cyanopyrid-2-yl)-urea, (1R, 2R)-N-[cis-2-(6-fluoro, 2-hydroxy, 3-acetylphenyl)-cyclopropyl]-N'-(5-cyanopyrid-2-yl)-urea, (1R, 2R)-N-[cis-2-(2-(3-aminophenylcarbonyloxy)-6-fluoro-3-propionylphenyl)-cyclopropyl]-N'-(5-cyanopyrid-2-yl)-urea;

(1R, 2R)-N-[cis-2-(2-(3-aminophenylcarbonyloxy)-6-fluoro-3-butyrylphenyl)-cyclopropyl]-N'-(5-cyanopyrid-2-yl)-urea;

(1R, 2R)-N-[cis-2-(2-(3-aminophenylcarbonyloxy)-6-fluoro-3-acetylphenyl)-cyclopropyl]-N'-(5-cyanopyrid-2-yl)-urea;

(1R, 2R)-N-[cis-2-(2-(3-ethylaminophenylcarbonyloxy)-6-fluoro-3-propionylphenyl)-cyclopropyl]-N'-(5-cyanopyrid-2-yl)-urea;

(1R, 2R)-N-[cis-2-(2-(3-ethylaminophenylcarbonyloxy)-6-fluoro-3-butyrylphenyl)-cyclopropyl]-N'-(5-cyanopyrid-2-yl)-urea;

(1R, 2R)-N-[cis-2-(2-(3-ethylaminophenylcarbonyloxy)-6-fluoro-3-acetylphenyl)-cyclopropyl]-N'-(5-cyanopyrid-2-yl)-urea;

(1R,2R)-N-[cis-2-(2-(3-dimethylaminophenylcarbonyloxy)-6-fluoro-3-propionylphenyl)-cyclopropyl]-N'-(5-cyanopyrid-2-yl)-urea;

(1R, 2R)-N-[cis-2-(2-(3-dimethylaminophenylcarbonyloxy)-6-fluoro-3-butyrylphenyl)-cyclopropyl]-N'-(5-cyanopyrid-2-yl)-urea;

(1R, 2R)-N-[cis-2-(2-(3-dimethylaminophenylcarbonyloxy)-6-fluoro-3-acetylphenyl)-cyclopropyl]-N'-(5-cyanopyrid-2-yl)-urea;

and their pharmaceutically acceptable salts.

Other convenient compounds include;

(1R, 2R)-N-[cis-2-(2-(6-methylaminopyrid-3-ylcarbonyloxy)-6-fluoro-3-propionylphenyl)-cyclopropyl]-N'-(5-cyanopyrid-2-yl)-urea;

(1R, 2R)-N-[cis-2-(2-(6-methylaminopyrid-3-ylcarbonyloxy)-6-fluoro-3-butyrylphenyl)-cyclopropyl]-N'-(5-cyanopyrid-2-yl)-urea;

(1R, 2R)-N-[cis-2-(2-(6-methylaminopyrid-3-ylcarbonyloxy)-6-fluoro-3-acetylphenyl)-cyclopropyl]-N'-(5-cyanopyrid-2-yl)-urea;

(1R, 2R)-N-[cis-2-(2-(6-aminopyrid-3-ylcarbonyloxy)-6-fluoro-3-propionylphenyl)-cyclopropyl]-N'-(5-cyanopyrid-2-yl)-urea;

(1R, 2R)-N-[cis-2-(2-(6-aminopyrid-3-ylcarbonyloxy)-6-fluoro-3-butyrylphenyl)-cyclopropyl]-N'-(5-cyanopyrid-2-yl)-urea;

(1R, 2R)-N-[cis-2-(2-(6-aminopyrid-3-ylcarbonyloxy)-6-fluoro-3-acetylphenyl)-cyclopropyl]-N'-(5-cyanopyrid-2-yl)-urea;

and pharmaceutically acceptable salts thereof.

Preferred compounds of the invention include (1S, 2S)-N-[cis-2-(2-(6-fluoro, 2-hydroxy, 3-propionylphenyl)-cyclopropyl]-N'-(5-bromopyrid-2-yl)-urea;

(1S, 2S)-N-[cis-2-(2-(3-aminophenylcarbonyloxy)-6-fluoro-3-propionylphenyl)-cyclopropyl]-N'-(5-bromopyrid-2-yl)-urea;

(1S, 2S)-N-[cis-2-(2-(3-aminophenylcarbonyloxy)-6-fluoro-3-acetylphenyl)-cyclopropyl]-N'-(5-bromopyrid-2-yl)-urea;

(1S, 2S)-N-[cis-2-(2-(3-aminophenylcarbonyloxy)-6-fluoro-3-butyrylphenyl)-cyclopropyl]-N'-(5-bromopyrid-2-yl)-urea;

(1S, 2S)-N-[cis-2-(2-(3-ethylaminophenylcarbonyloxy)-6-fluoro-3-propionylphenyl)-cyclopropyl]-N'-(5-bromopyrid-2-yl)-urea;

(1S, 2S)-N-[cis-2-(2-(3-ethylaminophenylcarbonyloxy)-6-fluoro-3-acetylphenyl)-cyclopropyl]-N'-(5-bromopyrid-2-yl)-urea;

(1S, 2S)-N-[cis-2-(2-(3-ethylaminophenylcarbonyloxy)-6-fluoro-3-butyrylphenyl)-cyclopropyl]-N'-(5-bromopyrid-2-yl)-urea;

(1S, 2S)-N-[cis-2-(2-(3-dimethylaminophenylcarbonyloxy)-6-fluoro-3-propionylphenyl)-cyclopropyl]-N'-(5-bromopyrid-2-yl)-urea;

(1S, 2S)-N-[cis-2-(2-(3-dimethylaminophenylcarbonyloxy)-6-fluoro-3-acetylphenyl)-cyclopropyl]-N'-(5-bromopyrid-2-yl)-urea;

(1S, 2S)-N-[cis-2-(2-(3-dimethylaminophenylcarbonyloxy)-6-fluoro-3-butyrylphenyl)-cyclopropyl]-N'-(5-bromopyrid-2-yl)-urea;

(1R, 2R)-N-[cis-2-(2-(6-fluoro, 2-hydroxy, 3-propionylphenyl)-cyclopropyl]-N'-(5-bromopyrid-2-yl)-urea;

(1R, 2R)-N-[cis-2-(2-(3-aminophenylcarbonyloxy)-6-fluoro-3-propionylphenyl)-cyclopropyl]-N'-(5-bromopyrid-2-yl)-urea;

(1R, 2R)-N-[cis-2-(2-(3-aminophenylcarbonyloxy)-6-fluoro-3-acetylphenyl)-cyclopropyl]-N'-(5-bromopyrid-2-yl)-urea;

(1R, 2R)-N-[cis-2-(2-(3-aminophenylcarbonyloxy)-6-fluoro-3-butyrylphenyl)-cyclopropyl]-N'-(5-bromopyrid-2-yl)-urea;

(1R, 2R)-N-[cis-2-(2-(3-ethylaminophenylcarbonyloxy)-6-fluoro-3-propionylphenyl)-cyclopropyl]-N'-(5-bromopyrid-2-yl)-urea;

(1R, 2R)-N-[cis-2-(2-(3-ethylaminophenylcarbonyloxy)-6-fluoro-3-acetylphenyl)-cyclopropyl]-N'-(5-bromopyrid-2-yl)-urea;

(1R, 2R)-N-[cis-2-(2-(3-ethylaminophenylcarbonyloxy)-6-fluoro-3-butyrylphenyl)-cyclopropyl]-N'-(5-bromopyrid-2-yl)-urea;

(1R, 2R)-N-[cis-2-(2-(3-dimethylaminophenylcarbonyloxy)-6-fluoro-3-propionylphenyl)-cyclopropyl]-N'-(5-bromopyrid-2-yl)-urea;

(1R, 2R)-N-[cis-2-(2-(3-dimethylaminophenylcarbonyloxy)-6-fluoro-3-acetylphenyl)-cyclopropyl]-N'-(5-bromopyrid-2-yl)-urea;

(1R, 2R)-N-[cis-2-(2-(3-dimethylaminophenylcarbonyloxy)-6-fluoro-3-butyrylphenyl)-cyclopropyl]-N'-(5-bromopyrid-2-yl)-urea;

and their pharmaceutically acceptable salts.

Further preferred compounds include:

(1S, 2S)-N-[cis-2-(2-(6-methylaminopyrid-3-ylcarbonyloxy)-6-fluoro-3-propionylphenyl)-cyclopropyl]-N'-(5-bromopyrid-2-yl)-urea;

(1S, 2S)-N-[cis-2-(2-(6-methylaminopyrid-3-ylcarbonyloxy)-6-fluoro-3-butyrylphenyl)-cyclopropyl]-N'-(5-bromopyrid-2-yl)-urea;

(1S, 2S)-N-[cis-2-(2-(6-methylaminopyrid-3-ylcarbonyloxy)-6-fluoro-3-acetylphenyl)-cyclopropyl]-N'-(5-bromopyrid-2-yl)-urea;

(1S, 2S)-N-[cis-2-(2-(6-aminopyrid-3-ylcarbonyloxy)-6-fluoro-3-propionylphenyl)-cyclopropy]-N'-(5-bromopyrid-2-yl)-urea;

(1S, 2S)-N-[cis-2-(2-(6-aminopyrid-3-ylcarbonyloxy)-6-fluoro-3-butyrylphenyl)-cyclopropyl]-N'-(5-bromopyrid-2-yl)-urea;

(1S, 2S)-N-[cis-2-(2-(6-aminopyrid-3-ylcarbonyloxy)-6-fluoro-3-acetylphenyl)-cyclopropyl]-N'-(5-bromopyrid-2-yl)-urea;

(1R, 2R)-N-[cis-2-(2-(6-methylaminopyrid-3-ylcarbonyloxy)-6-fluoro-3-propionylphenyl)-cyclopropyl]-N'-(5-bromopyrid-2-yl)-urea;

(1R, 2R)-N-[cis-2-(2-(6-methylaminopyrid-3-ylcarbonyloxy)-6-fluoro-3-butyrylphenyl)-cyclopropyl]-N'-(5-bromopyrid-2-yl)-urea;

(1R, 2R)-N-[cis-2-(2-(6-methylaminopyrid-3-ylcarbonyloxy)-6-fluoro-3-acetylphenyl)-cyclopropyl]-N'-(5-bromopyrid-2-yl)-urea;

(1R, 2R)-N-[cis-2-(2-(6-aminopyrid-3-ylcarbonyloxy)-6-fluoro-3-propionylphenyl)-cyclopropyl]-N'-(5-bromopyrid-2-yl)-urea;

(1R, 2R)-N-[cis-2-(2-(6-aminopyrid-3-ylcarbonyloxy)-6-fluoro-3-butyrylphenyl)-cyclopropyl]-N'-(5-bromopyrid-2-yl)-urea;

(1R, 2R)-N-[cis-2-(2-(6-aminopyrid-3-ylcarbonyloxy)-6-fluoro-3-acetylphenyl)-cyclopropyl]-N'-(5-bromopyrid-2-yl)-urea;

and pharmaceutically acceptable salts thereof.

Appropriate pharmaceutically acceptable salts of the compounds of formula I include salts of organic carboxylic acids such as acetic, lactic, gluconic, citric, tartaric, maleic, malic, pantothenic, isethionic, oxalic, lactobionic, and succinic acids, organic sulfonic acids such as methanesulfonic acid, ethanesulfonic acid, benzenesulfonic acid, p-chlorobenzenesulfonic acid and p-toluenesulfonic acid; and inorganic acids such as hydrochloric, hydroiodic, sulfuric, phosphoric and sulfamic acids.

In keeping with the usual practice with HIV inhibitors it is advantageous to co-administer one to three additional antivirals to provide synergistic responses and to ensure complementary resistance patterns. Such additional antivirals may include AZT, ddI, ddC, D4T, 3TC, abacavir, adefovir, adefovir dipivoxil, bis-POC-PMPA, foscarnet, hydroxyurea, HBY 097 (Hoechst-Bayer), efavirenz, trovirdine, nevirapine, delaviridine, PFA, H2G, ABT 606, DMP-450, loviride, ritonavir, saquinavir, indinavir, amprenavir, nelfinavir and the like, typically at molar ratios reflecting their respective activities and bioavailabilities. Generally such ratio will be of the order of 25:1 to 1:25, relative to the compound of formula I.

While it is possible for the active agent to be administered alone, it is preferable to present it as part of a pharmaceutical formulation. Such a formulation will comprise the above defined active agent together with one or more acceptable carriers and optionally other therapeutic ingredients. The carrier(s) must be acceptable in the sense of being compatible with the other ingredients of the formulation and not deleterious to the recipient.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate and other metallic stearates, stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

Convenient carriers for oral dosing include liquid formulations in the form of solutions, suspensions or emulsions, optionally encapsulated or otherwise presented in unit dose form in a conventional manner. Favoured formulations include acacia/TWEEN/water, TWEEN/water, propylene glycol, vegetable oil (such as peanut, safflower, olive and the like) with 10–20% ethanol, vegetable oil/Capmul MGM, Capmul MCM/propylene glycol, methyl cellulose/water, vegetable oil/stearoyl monoester of glycerol, vegetable oil/monounsaturated fatty acid ester of glycerol and the like.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Formulations suitable for topical administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Formulations suitable for topical administration to the skin may be presented as ointments, creams, gels, and pastes comprising the active agent and a pharmaceutically active carrier. An exemplary topical delivery system is a transdermal patch containing the active agent. Other topical formulations include antiseptic swabs which release the active agent upon the skin prior to invasive procedures such as injection or capillary blood sampling. Such swabs neutralise HIV in the blood or serum emanating from the invasive procedure thus assisting to prevent transfer of HIV to health care workers via needle stick accidents. Such swabs may comprise a sterile surgical gauze pad soaked in a solution of the active agent in a volatile solvent such as ethanol and single packed in a sealed sachet.

Formulations for rectal or vaginal administration may be presented as a suppository or pessary with a suitable base comprising, for example, cocoa butter or a salicylate. Other vaginal preparations can be presented as tampons, creams, gels, pastes, foams or spray formulations containing, in addition to the active agent, such carriers as are known in the art to be appropriate.

Formulations suitable for nasal administration wherein the carrier is a solid include a coarse powder having a particle size, for example, in the range 20 to 500 microns which is administered in the manner in which snuff is taken, i.e. by rapid inhalation from a container of the powder held up close to the nose. Suitable formulations wherein the carrier is a liquid for administration, for example, as a nasal spray or as nasal drops, include aqueous or oily solutions of the active agent.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in freeze-dried (lyophilized) condition requiring only the addition of the sterile liquid carrier, for example water for injection, immediately prior to use. Extemporaneous injection solutions and suspensions may be prepared from sterile powders, granules, and tablets of the kind previously described.

A further aspect of the invention provides methods for the preparation of the compounds of Formula I, in particular the cis enantiomers, comprising the Curtius rearrangement of a compound of the formula:

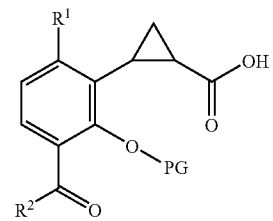

followed by coupling of a compound of the formula

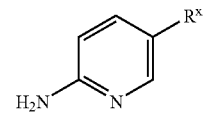

and deprotection, wherein $R^1$, $R^2$ and $R^x$ are as defined above and PG is an hydroxy-protecting group.

The methods of the invention can further comprise the step of acylating with an activated compound of the formula III:

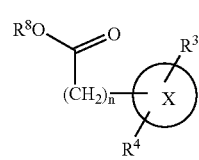

where $R^3$, $R^4$, X and n are as defined above but are optionally protected, and $R^8$ is hydrogen or a conventional activating group. Alternatively the method of the invention may further comprise the step of alkylation with a compound of the formula IIIa:

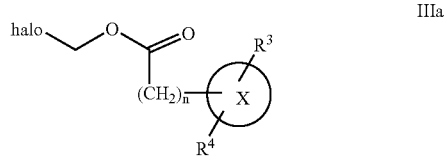

where n, $R^3$, $R^4$ and X are as defined above, but where exposed amine, hydroxy etc substituents being protected with conventional protecting groups.

Enantiomeric compounds of formula I may thus be prepared by the reaction scheme below:

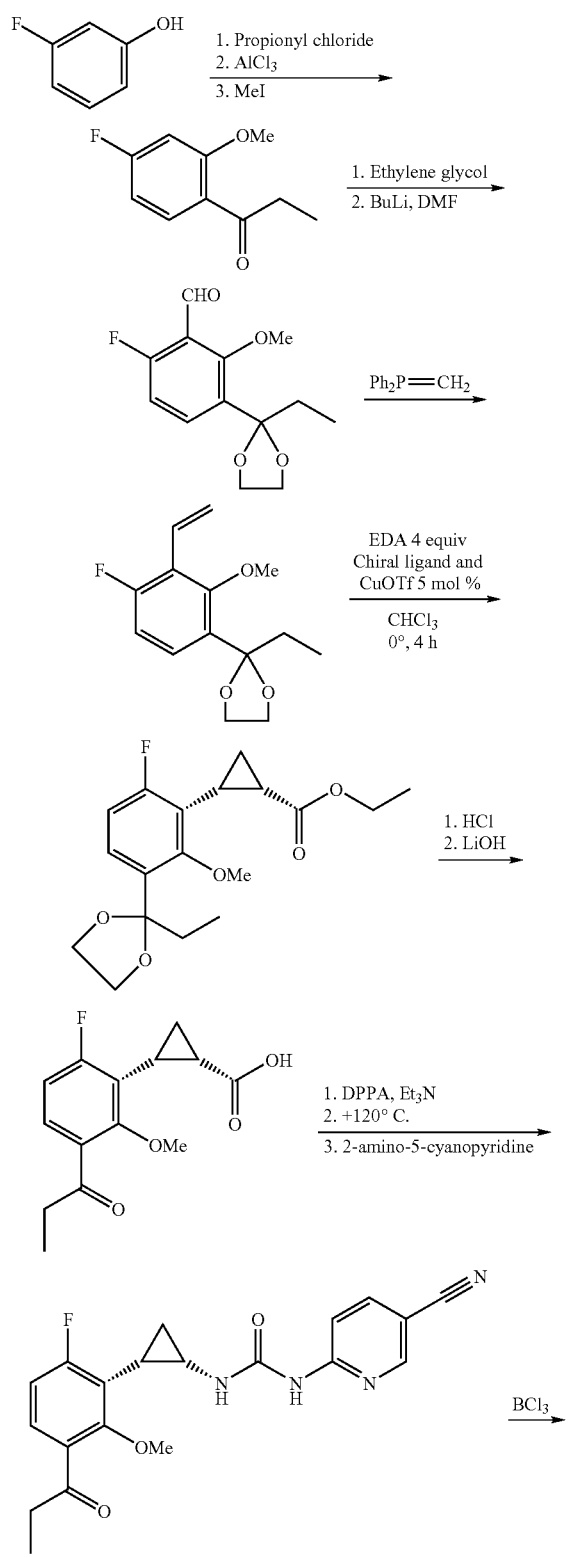

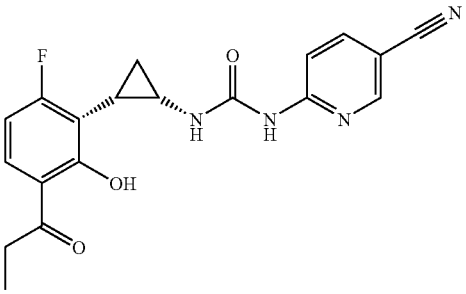

The above scheme illustrates the preparation of a (1S, 2S) compound of the invention where $R^x$ is cyano, $R^1$ is F and $R^2$ is ethyl, but corresponding methodology is applicable to the other $R^x$, $R^1$ and $R^2$ variants. The chiral ligand indicated for the fourth step may comprise, for example, a compound of the formula:

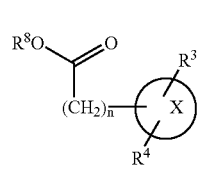

To prepare the 1R, 2R enantiomer, the mirror image chiral ligand is employed. Alternatively, the chiral ligand may be omitted in order to form the racemate.

Prodrugs of the formula II wherein p is 0 can be synthesised by acylating a compound of the formula I with with an activated compound of the formula III,

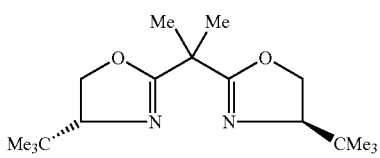

III where $R^3$, $R^4$, X and n are as defined above but are optionally protected, and $R^8$ is hydrogen or a conventional activating group.

Activated compounds of Formula III include the acid halide, acid anhydride, activated acid ester or the acid in the presence of a coupling reagent such as dicyclohexyl-carbodiimide. Representative activated acid derivatives include the acid chloride, formic and acetic acid derived mixed anhydrides, anhydrides derived from alkoxycarbonyl halides such as isobutyloxycarbonylchloride and the like, N-hydroxysuccinamide derived esters, N-hydroxyphthalimide derived esters, N-hydroxy-5-norbornene-2,3-dicarboxamide derived esters, 2,4,5-trichlorophenol derived esters and the like. Suitable optional protecting groups for compounds of formula III, especially any constituent amines, include those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference.

N-protecting groups include acyl groups such as formyl, acetyl, propionyl, pivaloyl, t-butylacetyl, 2-chloroacetyl, 2-bromoacetyl, trifluoracetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl gropus such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl, t-butoxycarbonyl (BOC) and benzyloxycarbonyl (Cbz).

The acylation is carried out with conventional esterification conditions such as DMAP and DCC in a solvent such as dimethylformamide or pyridine. Optional protecting groups may be removed with conventional techniques as comprehensively discussed in Greene above, such as TFA, HCl(aq)/dioxane or hydrogenation in the presence of a catalyst to give the compound of Formula II.

Compounds of the Formula II, wherein p is 1 can be prepared by reacting a compound of the formula III with iodochloromethane or mixed dichloro/iodochlor methane under conventional alkylating conditions to form a compound of the Formula IIIa:

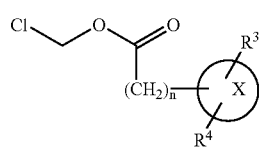

where n, $R^3$, $R^4$ and X are as defined above, but where exposed amine, hydroxy etc substituents being protected with conventional protecting groups. The compound of formula IIIa is then preferably converted to the corresponding iodo derivative by reaction with NaI followed by coupling to the compound of formula I, typically under basic conditions, such as an organic solvent containing sodium hydride.

DETAILED DESCRIPTION

Aspects of the invention will now be illustrated by way of example only with reference to the following non-limiting Examples and the Drawings in which.

Preparation of Intermediates

EXAMPLE 1

3-[1,1-(Ethylenedioxy)propyl]-6-fluoro-2-methoxybenzaldehyde

Figure 1:
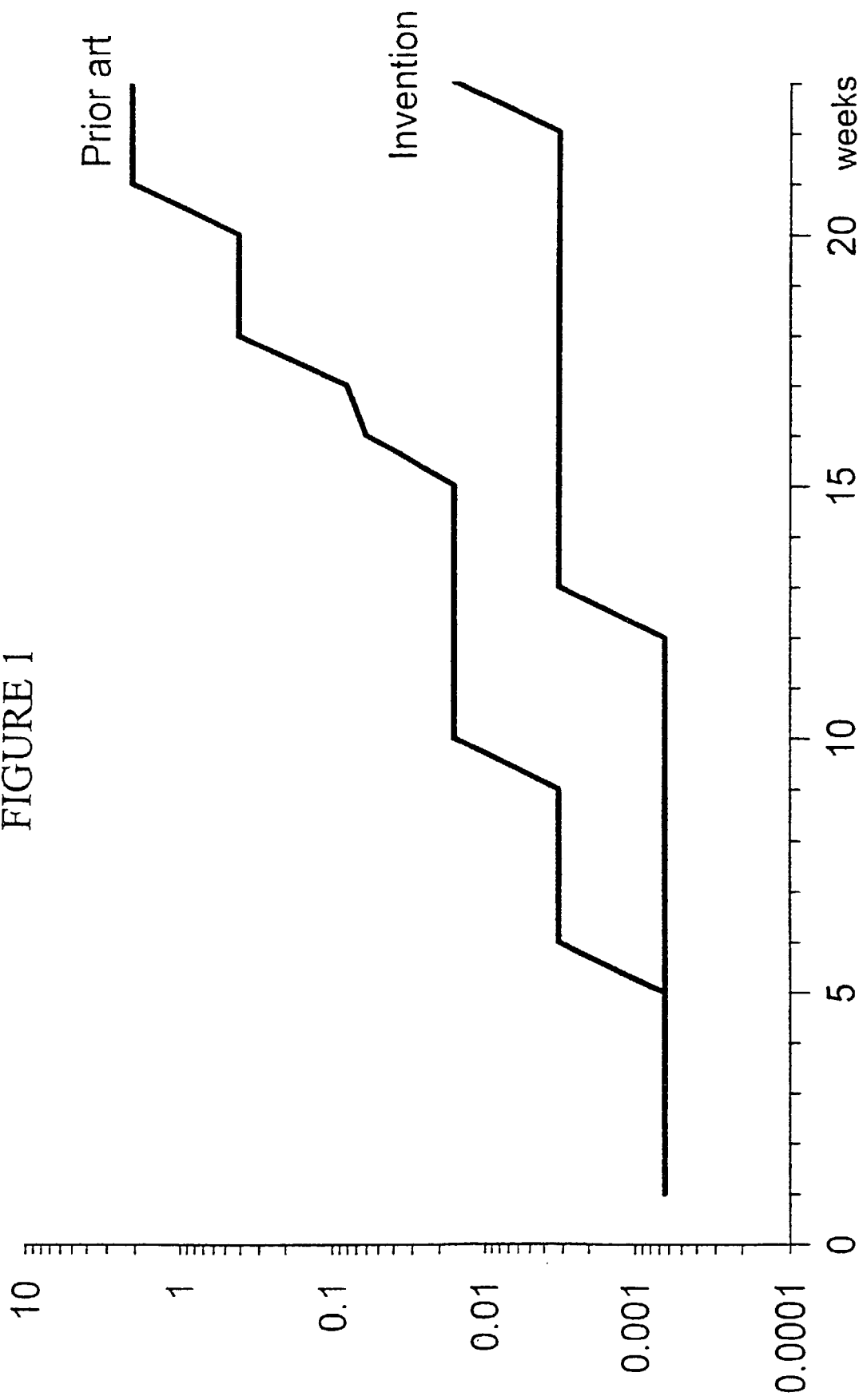
FIG. 1 depicts rate of resistance development against time for a compound of the invention in comparison to a prior art compound, as described in Biological Example 2.

To a solution of 3-fluorophenol (22.4 g, 0.2 mol), pyridine (24 ml, 0.3 mol) and dichloromethane (200 ml) at room temperature was added 20 ml (0.225 mol) propionyl chloride over a period of 5 min. The reaction was exothermic. The solution was stirred for another 30 min. After addition of dichloromethane, the organic phase was washed with sat. $NaHCO_3$ solution and water, dried over $MgSO_4$ and concentrated in vacuo. 33.8 g (100%) of 3-fluoro-1-propionyloxybenzene was obtained. This compound was reacted with 33.3 g (0.25 mol) $AlCl_3$ at 150° C. for a period of 10 min. After careful quenching with water, the reaction mixture was extracted three times with ether. The ether phase was dried ($MgSO_4$) and evaporated to give 29.5 g (0.176 mol, 88%) rearranged product. This intermediate was dissolved in 200 ml of acetone and $K_2CO_3$ (42, 0.3 mol) and MeI (25 ml, 0.4 mol) were added. The reaction mixture was heated at 40° C. for a period of 12 h. The reaction mixture was filtered and the acetone was evaporated. The residue was dissolved in ether and the ether phase washed with a 0.5 M NaOH solution and water. Drying ($MgSO_4$) and evaporation gave 31.2 g (0.17 mol, 86% yield for three steps) of 4-fluoro-2-methoxypropiophenone.

To a solution of 4-fluoro-2-methoxypropiophenone (31.2 g, 0.171 mol), ethylene glycol (10.5 ml, 0.188 mol) in benzene (300 ml) was added 1 g of p-toluenesulfonic acid. The reaction mixture was refluxed in a Dean-Stark apparatus for about 12 h. After cooling, the organic phase was washed several times with a 1 M NaOH solution and dried ($Na_2SO_4$ and $K_2CO_3$). The solvent was evaporated and about 38 g of the acetal was obtained. The purity according to capillary GC was 88% and the impurity was basically unreacted ketone. To a solution of the acetal in THF (450 ml) at −65° C. and under nitrogen was added droppwise 128 ml (0.32 mol) of 2.5 M n-BuLi. While keeping the temperature at about −65° C. a solution of DMF (25 ml, 0.32 mol) in THF (50 ml) was added. The reaction mixture was allowed to slowly reach room temperature and according to GC no starting material was left after about 30 min. After another 1 h, the reaction mixture was quenched with sat. $NH_4Cl$ solution and extracted three times with ether. After drying ($Na_2SO_4$) the residue was purified on a silica gel column (silica gel 60 from Merck, particle size 0.04–0.063 mm) eluting with EtOAc 1 and hexanes 9 to give 10 g (25%) of the title compound.

$^1$H NMR ($CDCl_3$) δ 0.85 (t, 3H), 2.1 (q, 2H), 3.8–3.95 (m, 2H), 3.97 (s, 4.15 (m, 2H), 6.9 (t, 1H), 7.7–7.8 (m, 1H), 10.4 (s, 11H).

EXAMPLE 2

3-[1,1-(Ethylenedioxy)propyl]-6-fluoro-2-methoxystyrene

To a suspension of methyltriphenylphosphonium bromide (14.3 g, 40 mmol) in THF (250 ml) at room temperature and under nitrogen was added 16 ml (40 mmol) of 2.5 M n-BuLi. To the almost obtained solution was then added 3-[1,1-(ethylenedioxy)propyl]-6-fluoro-2-methoxybenzaldehyde (10 g, 39.5 mmol) in THF (30 ml). The reaction mixture was then stirred at room temperature for 2 h and poured into a mixture of hexanes and brine. The organic phase was washed two times with brine and one time with water. After evaporation of the solvent, the residue was filtered through a funnel filled with alumina (aluminium oxide 90 acc. Brockmann from Merck) and eluting with EtOAc 1 and hexanes 9 in order to remove the formed triphenylphosphonium oxide. Evaporation of the organic solvent gave a residue which was finally purified on silica gel eluting with EtOAc 1 and hexanes 9 to give 6.9 g (70%) of the title compound with a purity of 94.5% as determined by capillary GC.

$^1$H NMR (250 Mhz, CDCl$_3$) δ 0.85 (t, 3H), 2.1 (q, 2H), 3.8 (s, 3H), 3.8–3.95 (m, 2H), 4.0–4.1 (m, 2H), 5.55–5.65 (m, 1H), 5.95–6.05 (m, 1H), 6.7–6.85 (m, 2H), 7.3–7.4 (m, 1H).

EXAMPLE 3

(1S, 2R)-cis-2-(6-fluoro-2-methoxy-3-propionylphenyl)cyclopropylcarboxylic acid

The ethyl ester of (1S, 2R)-cis-2-[3-(1,1-ethylenedioxy)ethyl-6-fluoro (2-methoxyphenyl)cyclopropylcarboxylic acid was prepared from 3-[1,1-(ethylenedioxy) propyl]-6-fluoro-2-methoxystyrene (19.4 g, 69 mmol) and ethyl diazoacetate (29 ml, 275 mmol) using a asymmetric cyclopropanation reaction catalyzed by Cu(I)triflate (679 mg, 1.35 mmol) and the chiral ligand ([2,2'-isopropylidenbis((4R)-4-tert-butyl-2-oxazoline)] (794 mg, 2.7 mmol) as generally described by Evans et al in *J.Am.Chem.Soc.* 1991, 113, 726–728. After silica gel chromatography, 9.4 g (40.5%) of the ethyl ester was obtained. The enantiomeric excess was 99% as determined by HPLC on a chiral column. The ester was dissolved in 150 ml of dioxane and 30 ml of 6M HCl was added. The reaction mixture was stirred over night and partitioned between ether and brine. The solvent was evaporated to give 19 g of crude produkt. This product was dissolved in methanol (250 ml) and water (75 ml) and 6 g (250 mmol) of LiOH was added. The reaction mixture was heated to 90° C. for 24 h and most of the solvent was evaporated. The remaining mixture was acidified and extracted three times with dichloromethane. Evaporation of the solvent afforded 11.2 g of the title compound.

$^1$H-NMR (250 MHz, CDCl$_3$) δ 1.15 (t, 3H), 1.59 (t, 2H), 2.10–2.17 (m, 1H), 2.22–2.32 (m, 1H), 2.91 (q, 2H), 3.80 (st, 3H), 6.82 (t, 1H), 7.44–7.50 (m, 1H), 11.30 (broad s, 1H).

EXAMPLE 4

(1R,2 S)-cis-2-(6-fluoro-2-methoxy-3-propionylphenyl)Cyclopropylcarboxylic Acid

This compound was prepared from 3-[1,1-ethylenedioxy) propyl]-6-fluoro-2-methoxystyrene as described for the acid in Example 3. The chiral ligand which was used was 2,2'-isopropylidenebis[(4S)-4-tert-butyl-2-oxazoline].

$^1$H NMR (250 Mhz, CDCl$_3$) δ 7.48 (q, 1H), 6.84 (t, 1H), 3.82 (s, 3H), 2.93 (q, 2H), 2.29 (q, 1H), 2.14 (q, 1H), 1.60 (m, 2H), 1.16 (t, 3H).

Preparation of Compounds of Formula I and II

EXAMPLE 5

(±)N-[cis-2-(2-(6-fluoro-2-hydroxy-3-propionylphenyl)-cyclopropyl]-N'-(5-cyanopyrid-2-yl)-urea A solution of 3-[1,1-(ethylenedioxy)propyl]-6-fluoro-2-methoxystyrene (32.4 g, Example 2) and copper bromide-dimethyl sulfide complex (0.30 g) in dichloroethane (200 ml) was heated to 80° C. under nitrogen. Ethyl diazoacetate (54 ml) in dichloroethane (600 ml) was added during 7 h. After the addition was complete the heating was turned off. After 16 h the solvent was evaporated and the residue was purified on silica gel eluting with ethyl acetate and hexanes to give the cis-ester (6.5 g)

The cis-ester (3.7 g, 10.9 mmol) was dissolved in ethanol (20 ml) and KOH (1.8 g, 32.7 mmol) was dissolved in water (10 ml). The solutions were combined and heated to reflux for 3 h. Water (30 ml) was added and the solution was washed twice with hexanes (20 ml). The water phase was cooled in an ice bath and acidified with dilute HCl. The solution was extracted three times with toluene. The toluene phase was dried (MgSO$_4$) and evaporated to give 1.9 g (±)-cis-2-[3-(1,1-ethylenedioxypropyl)-6-fluoro-2-methoxyphenyl]cyclopropylcarboxylic acid.

Triethylamine (59 μl, 0.43 mmol) and diphenylphosphoryl azide (92 μl, 0.43 mmol) was added to a solution of the acid (120 mg, 0,39 mmol) in dry toluene. The solution was stirred at room temperature for 1 h and then heated to 120° C. After 1 h 2-Amino-5-cyanopridine (51 mg, 0.43 mmol) was added. Heating was maintained for an additional 3 h. After 16 h the solvent was evaporated, the residue was dissolved in dichloromethane (30 ml), washed with dilute HCl, dried (MgSO$_4$) and evaporated to give 152 mg. This product was dissolved in dioxane and HCl (6N, 1 ml) was added. After 2 h the mixture was evaporated, dissolved in dichloromethane (25 ml), washed with water (10+10 ml), dried (MgSO$_4$) and evaporated to give 117 mg. The residue was purified on silica gel eluting with ethyl acetate and hexanes to give 37 mg 2-methoxyphenyl intermediate product.

A 1M solution of boron tribromide in dichloromethane (194 μl, 0.194 mmol) was added to a solution of the 2-methoxyphenyl intermediate (37 mg, 0.097 mmol) in dichloromethane at −60° C. After 10 min the cooling bath was removed and the stirring was continued for 2 h. The solution was diluted with dichloromethane, washed with dilute NaHCO$_3$ and water, dried (MgSO$_4$) and evaporated. The residue was recrystallized from MeCN giving 17 mg of the title product.

$^1$H-NMR (250 MHz, DMSO-d$_6$) δ 1.07–1.16 (m,4H), 1.41–1.50 (m, 1H), 1.91–2.01 (m, 1H), 3.06–3.19 (m, 3H), 6.86 (dd, 1H), 7.43 (d, 1H), 7.80–7.90 (m, 1H), 7.97–8.08 (m, 2H), 8.32 (d, 1H), 9.83 (s, 1H), 13.2 (d, 1H).

EXAMPLE 6

(1R,2R)-N-(cis-2-(6-fluoro-2-hydroxy-3-propionylphenyl)-cyclopropyl)-N'-(5-cyanopyridy-2-yl)-urea Triethylamine (0.85 mL, 6.1 mmol) and diphenyl phosphoryl azide (1.72 g, 6.1 mmol) was added to a solution of the acid prepared in Example 4 (1.47 g, 5.5 mmol) in dry toluene (15 mL). The solution was stirred at room temperature under argon for 30 min and then heated to 120° C. After 15 min a solution of 2-amino-5-cyanopyridine (0.99 g, 8.9 mmol) in DMF (3 mL) was added and heating was continued for 4 h. Toluene was evaporated, and the mixture was diluted with diethyl ether (100 mL) and ethyl acetate (50 mL) and washed with 1 M HCl, $H_2O$ and brine. The organic layer was dried ($Na_2SO_4$) and concentrated. The residue was purified with silica gel flash column chromatography by eluting with ethyl acetate/n-hexane 1:10 to 1:1 to give 1.6 g (66%) of the 2-methoxyphenyl intermediate.

A 1 M solution of boron trichloride in $CH_2Cl_2$ (11.0 mL, 11.0 mmol) was added to a solution of the 2-methoxyphenyl intermediate (1.40 g, 3.66 mmol) in $CH_2Cl_2$ (80 mL) at $-72°$ C. under argon. After 10 min the cold bath was removed and the stirring was continued for 1 h 15 min. The solution was diluted with $CH_2Cl_2$ and washed with an aqueous solution of $NaHCO_3$, $H_2O$ and brine. The organic layer was dried ($Na_2SO_4$) and concentrated. The precipitate from acetonitrile/$H_2O$ 1:1 gave 0.62 g of pure title compound. The residue was concentrated and the chromatography by eluting with ethyl acetate/n-hexane 1:10 to 1:1 and ethyl acetate, and then crystallization from acetonitrile gave 0.2 g of the title product. The yield 0.82 g (61%). The ee was 95% as determined by HPLC on a chiral column. $[\alpha]_d^{22}$ $-171.2°$ (c=0.50, $CH_2Cl_2$)

$^1$H NMR (250 Mhz, $CDCl_3$) δ 13.35 (d, 1H), 10.02 (br s, 1H), 9.40 (br s, 1H), 8.11 (s, 1H), 7.71 (m, 2H), 7.00 (m, 1H), 6.61 (t, 1H), 3.21 (m, 1H), 3.01 (q, 2H), 2.03 (m, 2.03 (m, 1H), 1.55 (m, 1H), 1.29 (m, 4H).

EXAMPLE 7

(1R, 2R)-N-[cis-2-(2-(3-aminophenylcarbonyloxy)-6-fluoro-3-propionylphenyl)-cyclopropyl]-N'-(5-cyanopyrid-2-yl)-urea To a solution of the compound described in Example 6 (1.64 g, 4.4 mmol), BOC-protected 3-aminobenzoic acid (1.6 g, 6.6 mmol) and 4-dimethylaminopyridine (269 mg, 2.2 mmol) in 20 ml of dichloromethane and 10 ml of DMF at room temperature and under argon was added 1.36 g (6.6 mmol) of DCC. The reaction mixture was stirred for 24 hrs. The solvent was carefully evaporated and the residue purified on silica gel using hexanes/ethyl acetate 1:1 as the solvent to give 2.6 g of BOC-protected title product. This product was added to 75 ml trifluoroacetic acid at 0° C. The mixture was then stirred at 0° C. for 1 hour. The solvent was carefully removed in vacuo. The residue was partitioned between ethylacetate and sat. potassium carbonate. The organic phase was dried and evaporated. The residue was purified on a silica gel column using ethyl acetate/hexanes 4:1 as eluent to give 1.03 g of the free base of the title compound. This intermediate was treated with 3 ml 1M HCl in ether and 0.84 g of the titled compound was achieved. The HPLC purity was about 97%.

$^1$H-NMR liberated amine (250 MHz, $CDCl_3$) δ 1.09 (t, 3H), 1.2–1.3 (m, 1H), 1.4–1.5 (m, 1H), 1.95–2.00 (m, 1H), 2.83 (q, 2H), 3.15–3.25 (m, 1H), 3.85 (s, 2H), 6.90 (dd, 2H), 7.09 (t, 1H), 7.20–7.27 (m, 1H), 7.44–7.46 (m, 1H), 7.56 (dd, 1H), 7.67–7.77 (m, 2H), 8.13 (d, 1H), 9.1 (broad s, 1H), 9.6 (broad s, 1H).

EXAMPLE 8

(1 S,2S)-N-(cis-2-(6-fluoro-2-hydroxy-3-propionoylphenyl)-cyclopropyl)-N'-(5-cyanopyrid-2-yl)-urea Triethylamine (670 μl, 4.8 mmol) and diphenyl phosphoryl azide (1.05 ml, 4.9 mmol) were added to a solution of the acid prepared in example 3 (1.2 g, 4.5 mmol) in dry toluene (10 ml) under nitrogen. The solution was stirred at room temperature for 30 min. and then heated to 120° C. After 15 min. a solution of 2-amino-5-cyanopyridine (0.80 g, 6.7 mmol) in dimethyl formamide (1.5 ml) was added and the heating was continued for 4 h. The solution was diluted with diethyl ether and washed with 1M hydrochloric acid. The organic layer was dried ($MgSO_4$) and concentrated. The residue was purified by silica gel flash chromatography (gradient starting with n-hexane:ethyl acetate 1:1, finishing with pure ethyl acetate) giving slightly unpure 2-methoxyphenyl derivative (0.93 g). Repeated chromatography, as described above, gave the pure 2-methoxyphenyl derivative. (0.70 g, 41%).

A 1M solution of boron trichloride in methylene chloride (5.5 ml, 5.5 mmol) was added to a solution of the 2-methoxyphenyl intermediate (700 mg, 1.8 mmol) in methylene chloride at $-60°$ C. After 10 min. the cold bath was removed and the stirring continued for 2 h. The solution was diluted with methylene chloride and washed with an aqueous solution of sodium hydrogen carbonate. The organic layer was dried ($MgSO_4$) and concetrated and the residue was purified by silica gel flash chromatography (gradient, n-hexane:ethyl acetate 2:1, 1:1, 1:2, ethyl acetate:methanol (8:1) giving the title compound (500 mg, 74%). $[\alpha]_D^{22}$+165.0° (C=0.5, $CH_2Cl_2$).

$^1$H-NMR (DMSO-$d_6$) δ 1.10–1.16 (m, 4H, $CH_3$, $CH_2$-cyclopropyl), 1.45 (dd, 1H, $CH_2$-cyclopropyl), 1.96 (q, 1H, CH-cyclopropyl), 3.10–3.19 (m, 3H, CH-cyclopropyl, $CH_2$), 6.85 (t, 1H, Ar), 7.43 (d, 1H, Ar), 7.86–8.07 (m, 3H), 8.32 (s, 1H), 9.83 (s, 1H), 13.22 (s, 1H, Ar—OH).

EXAMPLE 9

(1S, 2S)-N-[cis-2-(2-(3-aminophenylcarbonyloxy)-6-fluoro-3-propionylphenyl)-cyclopropyl]-N'-(5-cyanopyrid-2-yl)-urea Starting from the compound described in Example 6 and using the method described in Example 7 gave the titled product as the hydrochloride salt.

$^1$H-NMR (250 MHz, DMSO-$d_6$) δ 0.94 (t, 3H), 0.9–1.0 (m, 1H), 1.3–1.4 (m, 1H), 1.85–1.95 (m, 1H), 2.91 (q, 2H), 3.05–3.15 (m, 1H), 7.4–7.5 (m, 2H), 7.6–7.7 (m,1H), 7.9–8.1 (m, 5H), 8.08 (d, 1H), 9.85 (s, 1H).

EXAMPLE 10

(1S, 2S)-N-(cis-2-(6-fluoro-2-hydroxy-3-propionylphenyl)-cyclopropyl)-N'-(5-bromopyrid-2-yl)-urea (1S, 2R)-cis-2-(6-fluoro 2-methoxy-3-propionylphenyl) cyclopropylcarboxylic acid (3.0 g, 11.3 mmol), triethylamine (1.58 ml, 11.3 mmol)and diphenylphosphoryl azide (2.44 ml, 11.3 ml) were dissolved in dry toluene (8 ml) at room temperature and under an atmosphere of argon. The reaction mixture was stirred at room temperature for a period of 30 min whereafter the the temperature was increased to 120° C. and kept there for another 15 min. Then, 2-amino-5-bromopyridine (2.08 g, 12 mmol) was added and the reaction mixture was stirred at 120° C. for 2.5 hrs. Benzene and 1M HCl solution were added and the organic phase was evaporated. The residue was purified on silica gel using hexanes:ethyl acetate 1:1 as the eluent. The appropriate fractions were collected and 5.0 g of (1S, 2S)-N-(cis-2-(6-fluoro-2-methoxy-3-propionyl-phenyl)-cyclopropyl)-N'-

(5-bromopyrid-2-yl)-urea was obtained. This compound was dissolved in dichloromethane (100 ml) and the solution was kept under argon and cooled to −65° C. Boron trichloride (30 ml of a 1M solution in dichloromethane, 30 mmol) was added and the reaction mixture was allowed to reach room temperature over night. Dichloromethane and sat. sodium bicarboante were added. The organic phase was evaporated and the residue purified on silica gel using ethyl acetate:methanol 9:1 as the eluent. 1.96 g (41%) of the title compound was obtained.

Analysis: Calculated: C 51.2, H 4.1, N 9.9. Found: C 51.5, H 3.7, N 9.5.

Mp: 198–199° C. $[\alpha]_D^{22}$+149.8° (c=0.50, $CH_2Cl_2$)

$^1$H-NMR (250 MHz, $CDCl_3$) δ 1.28 (t, 3H), 1.52–1.62 (m, 2H), 1.94–2.05 (m, 1H), 2.97–3.06 (m, 2H), 3.17–3.20 (m, 1H), 6.60 (t, 1H), 6.76 (broad s, 1H), 7.57 (dd, 1H), 7.67–7.72 (m, 1H),7.83 (broad s, 1H) 8.53 (broad s, 1H), 13.32 (d, 1H).

EXAMPLE 11

(1R, 2R)-N-(cis-2-(6-fluoro-2-hydroxy-3-propionylphenyl)-cyclopropyl)-N'-(5-bromopyridyl-2-yl)-urea An asymmetric cyclopropanation reaction, as described in Example 3, was performed on the compound described in Example 2 using the chiral ligand 2,2'-isopropylidinebis (4S)-4-tert-butyl-2-oxazoline (commercially available from Aldrich). The obtained (1R, 2S)-cis-2-(6-fluoro-2-methoxy-3-propionylphenyl)cyclopropylcarboxylic acid was then used in a manner analogous to Example 10 to give the title compound.

$^1$H-NMR (250 MHz, DMSO-$d_6$) δ 1.05–1.15 (m, 1H), 1.12 (t, 3H), 1.40–1.50 (m, 1H), 1.90 (q, 1H), 3.00–3.10 (m, 1H), 3.12 (q, 2H), 6.82 (t, 1H), 7.18 (d, 1H), 7.78 (dd, 1H), 7.88 (broad s, 1H), 7.95–8.05 (m, 1H), 9.41 (broad s, 1H), 13.20 (s, 1H). $[\alpha]_D^{22}$−153.8° (c=0.50, $CH_2Cl_2$)

EXAMPLE 12

(1S, 2S)-N-[cis-2-(2-(3-aminophenylcarbonyloxy)-6-fluoro-3-propionylphenyl)cyclopropyl]-N'-(5-bromopyrid-2-yl)-urea To a solution of the compound of example 10 (633 mg, 1.5 mmol), BOC-protected 3-aminobenzoic acid (475 mg, 2 mmol) and 4-dimethylaminopyridine (123 mg, 1 mmol) in 20 ml of dichloromethane:DMF 1:1 at room temperature and under argon was added 415 mg (2 mmol) of DCC. The reaction mixture was stirred for 36 hrs. The solvent was carefully evaporated and the residue purified on silica gel using hexanes:ethyl acetae 1:1 as the solvent to give 811 mg of BOC-protected title product. This product was dissolved in dioxane (20 ml) and 10 ml 6M HCl was added and the mixture stirred over night. The solvent was carefully removed in vacuo. The residue was treated with ethanol and ether and 255 mg of the titled product was obtained as the HCl salt. The HPLC purity was about 93%.

$^1$H-NMR (250 MHz, $CD_3OD$) δ 1.15 (t, 3H), 1.3–1.4 (m, 1H), 1.5–1.6 (m, 1H), 2.05–2.15 (m, 3H), 3.04 (q, 2H), 3.23–3.27 (m, 1H), 7.16 (d, 1H), 7.34 (t, 1H), 7.85–7.93 (m, 2H), 8.05 (dd, 1H, 8.19(broad d, 1H), 8.26 (broad s, 1H), 8.35–8.37 (m, 1H), 8.42–8.46 (m, 1H).

EXAMPLE 13

(1S, 2S)-N-[cis-2-(2-(3-L-alanylaminophenylcarbonyloxy-6-fluoro-3-propionylphenyl)-cyclopropyl]-N'-(5-bromopyrid-2-yl)-urea The starting compound, BOC-protected 3-L-alanylaminobenzoic acid, was prepared from TCE-protected 3-aminobenzoic acid using standard chemistry, see for example Bodanszky's "The Practice of Peptide Synthesis" 2nd edition, Springer. This compound was reacted with the compound of Example 10 as described in Example 12 to give the title product as the HCl salt.

$^1$H-NMR (250 MHz, liberated amine, $CDCl_3$) δ 1.10 (t, 3H), 1.15–1.25 (m, 1H), 1.4–1.5 (m, 1H), 1.42 (d, 2H), 1.76 (broad s, 2H), 1.88–1.97 (m, 1H), 2.84 (q,2H) 3.1–3.2 (m, 1H), 3.59–3.67 (m, 1H), 6.78 (d, 1H), 7.09 (t, 1H), 7.85–7.93 (m, 2H), 8.08(d, 1H), 8.11 (s, 1H), 8.29 (broad s, 1H), 9.05 (broad s, 1H), 9.70 (broad s, 1H).

EXAMPLE 14

(1S,2S)-N-{cis-2-[6-fluoro-3-propionyl-2-(4-pyridylcarbonyloxy)phenyl]cyclopropyl}-N'-(5-bromopyrid-2-yl)urea In a manner analogous to Example 12, the product of Example 10 was condensed with isonicotinic acid to give the title product as the HCl salt.

$^1$H NMR (250 MHz, $CD_3OD$) δ 9.26 (d,2H), 8.83 (d,2H), 8.14 (m,2H), 8.04 (dd,1H), 7.39 (t,1H), 7.10 (d,1H), 3.38 (m,1H), 3.08 (m,2H), 2.15 (m,1H), 1.62 (m,1H), 1.38 (m,1H), 1.13 (t,3H).

EXAMPLE 15

(1S,2S)-N-{cis-2-[2-(3-dimethylaminophenylcarbonyloxy)-6-fluoro-3-propionylphenyl]cyclopropyl}-N'-(5-bromopyrid-2-yl)urea In a manner analogous to Example 12, the product of Example 10 was condensed with 3-dimethylaminobenzoic acid to give the title product as the HCl salt.

$^1$H NMR (250 MHz, $CD_3OD$) δ 8.61 (s,1H), 8.45 (d,1H), 8.15–8.03 (m,4H), 7.92 (t,1H), 734 (t,1H), 7.10 (d,1H), 3.48 (s,6H), 3.28 (m,1H), 3.00 (m,2H), 2.11 (m,1H), 1.58 (m,1H), 1.38 (m,1H), 1.14 (t,3H).

EXAMPLE 16

(1 S,2S)-N-[cis-2-(2-(3-aminomethylbenzoyloxymetyloxy)-5-fluoro-3-propionylphenyl)-cyclopropyl]-N'-(5-bromopyrid-2-yl)-urea 3-t-butoxycarbonylamidomethylbenzoic acid was treated with tetrabutyl ammonium hydroxide solution (1M in MeOH) to pH 9 and evaporated. The residue was dissolved in dichloromethane and was treated with chloroiodomethane overnight. The solution was washed with water and was evaporated to obtain crude 3-t-butoxycarbonylamidomethylbenzoyloxymethylchloride. This material was reacted with the sodium salt of Example 10 (prepared with sodium hydride in DMF) with a little sodium iodide as catalyst. After 2 hours reaction the solution was quenched with acetic acid and was diluted with dichloromethane, washed with water and evaporated. The crude product was purified on silica-gel by elution with ethylacetate/hexane 1:2 and the pure material was treated with trifluoroacetic acid and evaporated to obtain the trifluoroacetate salt of the title compound as a solid.

$^1$H NMR (CDCl$_3$) δ 1.1 (t, 3H) 1.3–1.5 (m,2H) 2.2 (q, 1H) 2.9 (m, 2H) 3.2 (bs, 1H) 4.2 (s, 2H) 5.9 (q, 2H) 6.8 (d, 2H) 7.0 (t, 1H) 7.3–8.1 (m, 9H).

EXAMPLE 17

(1S,2S)-N-(cis-2-(2-(3-amino-4-methylbenzoyloxy)-6-fluoro-3-propionylphenyl) cyclopropyl)-N'-(5-bromopyrid-2-yl)-urea (1S,2S)-N-(cis-2-(6-fluoro-2-hydroxy-3-propionylphenyl)-cyclopropyl)-N'-(5-bromopyrid-2-yl)-urea from Example 10 was condensed with 3-t-butoxycarbonylamido-4-methylbenzoic acid according to the procedure in Example 12. The product was treated with trifluoroacetic acid and was evaporated to obtain a the trifluoroacetic salt of the title compound as a solid.

$^1$H NMR (CDCl$_3$) δ 1.1 (t, 3H) 1.3–1.5 (m, 2H) 1.9 (q, 1H) 2.4 (s, 3H) 2.9 (q,2H) 3.1 (BS, 1H) 7.1 (t, 1H) 7.4 (d, 1H) 7.8 (m, 1H) 7.9 (m, 2H) 8.1 (s, 1H) 8.3 (s, 1H)

EXAMPLE 18

(1S,2S)-N-(cis-2-(2-(3-ethylaminobenzoyloxy)-6-fluoro-3-propionylphenyl cyclopropyl)-N'-(5-bromopyrid-2-yl)-urea The compound of Example 10 was condensed with 3-(N-ethyl-t-butoxy carbonylamido)benzoic acid according to the procedure in Example 12 and the product was treated with trifluoroacetic acid and evaporated to obtain the trifluoroacetic salt of the title compound as a solid.

$^1$H NMR (CDCl$_3$) δ 1.1 (t, 3H) 1.3–1.6 (m,5H) 2.9 (q, 2H) 3.1 (bs, 1H) 3.5 (q,2H) 7.1 (t, 1H) 7.2 (bs, 1H) 7.6 (t, 1H) 7.7–7.8 (m, 2H) 7.9 (d, 11H) 8.1 (s, 1H) 8.2 (d, 1H) 8.4 (s, 1H)

EXAMPLE 19

(1S,2S)-N-(cis-2-(2-quinolo-4-yloxy-6-fluoro-3-propionylphenyl) cyclopropyl)-N'-(5-bromopyrid-2-yl)-urea The compound of Example 10 was condensed with 4-quinolinic acid according to the procedure in Example 12 and the product was dissolved in trifluoroacetic acid and evaporated to obtain the acetic salt of the title compound as a solid.

$^1$H NMR (CDCl$_3$) δ 1.1 (t, 3H) 1.2 (m, 1H) 1.5 (m, 1H) 1.9 (m, 1H) 2.8 (q,2H) 3.2 (bs, 1H) 6.7 (d, 1H) 7.2 (t, 11H) 7.5 (m, 1H) 7.7 (t, 1H) 7.8–8.0 (m, 2H) 8.2 (d, 1H) 8.3 (d, 1H) 8.8 (d, 1H) 9.1 (m, 2H) 9.2 (bs, 1H)

EXAMPLE 20

(1S,2S)-N-(cis-2-(3-aminomethyl-2-methylbenzoyloxy)-fluoro-3-propionylphenyl) cyclopropyl)-N'-(5-bromopyrid-2-yl)-urea The compound of Example 10 was condensed with 3-t-butyloxycarbonyl amido-2-methylbenzoic acid according to the procedure in Example 12. The product was treated with trifluoroacetic acid and evaporated to yield the title compound as a solid.

$^1$H NMR (CDCl$_3$) δ 1.1 (t, 3H) 1.1–1.3 (m, 2H) 1.9 (m, 1H) 2.5 (s, 3H) 2.9 (q,2H) 3.1 (bs, 1H) 4.2 (s, 2H) 7.0–7.2 (m, 2H) 7.4 (d, 1H) 7.6–7.7 (m, 2H) 7.8–8.0 (m, 2H) 8.2 (bs, 2H)

EXAMPLE 21

(1S, 2S)-N-[cis-2-(6-fluoro-2-(4-aminomethylphenylcarbonyloxy)-3-propionylphenyl)-cyclopropyl]-N'-(5-bromopyrid-2-yl)-urea 4-(tert-butyloxycarbonylamidomethyl)benzoic acid was prepared by adding 6.5 g of DCC to a solution of 4 g 4-cyanobenzoic acid in 200 ml MeOH. The mixture was stirred 70 hours at room temperature, filtered to remove the precipitated dicyclohexylurea and the filtrate was concentrated in vacuo to yield 7 g a crude product. The methyl ester was dissolved in 500 ml MeOH and 9.6 g CoCl$_2$ 6H$_2$O was added. The mixture was treated portionwise with NaBH$_4$. After 5 h the reaction mixture was concentrated and the precipitate was removed. The filtrate was acidified with 150 ml 1M HCl (aq.) and extracted with 2×100 ml CH$_2$Cl$_2$. The acidic water phase was treated with 100 ml 25% NH$_3$ (aq.), extracted with 3×100 ml CH$_2$Cl$_2$, dried with Na$_2$SO$_4$ and concentrated to give 2.64 g brownish oil.

The oil was dissolved in 30 ml dioxane/water mixture (2:1) and treated for 20 hours with 1.5 g NaOH (s). Solvent was removed and 40 ml t-butanol/water mixture (1:1) added. The solution was stirred 24 hours after addition of 3.7 g di-tert-butyl dicarbonate, more water was then added and the mixture extracted with 2×50 ml hexane. The water phase was acidified (pH ~1.5–2.0) with NaHSO$_4$ and extracted with 3×75 ml ether. The pooled extracts were washed with 50 ml brine, dried with Na$_2$SO$_4$ and evaporated to yield the intermediate 4-(tert-butyloxycarbonyl-amidomethyl)benzoic acid as a white solid.

4-(tert-butyloxycarbonylamidomethyl)benzoic acid and (1S, 2S)-N-(cis-2-(6-fluoro-2-hydroxy-3-propionylphenyl)-cyclopropyl)-N'-(5-bromopyrid-2-yl)-urea from Example 10 were condensed and the BOC-protecting group removed using the method described in Example 12 to obtain the titled product as the hydrochloride salt.

$^1$H-NMR (250 MHz, CDCl$_3$) δ 0.98 (t, 3H), 1.05–1.20 (m, 1H), 1.31–1.49 (m, 1H), 1.69–1.90 (m, 1H), 2.65 (q, 2H), 3.33–3.49 (m, 1H), 4.31 (broad s, 2H), 7.02–7.22 (m, 2H), 7.35–7.49 (m, 1H), 7.50–7.68 (m, 2H), 7.69–7.83 (m, 2H), 8.08 (d, 1H) 8.37 (broad s, 1H).

EXAMPLE 22

(1S, 2SR)-N-[cis-2-(6-fluoro-2-(N-methylindol-5-carbonyloxy)-3-propionylphenyl)-cyclopropyl]-N'-(5-bromopyrid-2-yl)-urea i) Preparation of N-methylindol-5-carboxylic acid 0.1 g of indol-5-carboxylic acid was mixed with 2 equivalents of methyl trifluoromethane sulfonate in 1 ml DMF at room temperature. After 5 h the solvent was evaporated and $^1$H-NMR was recorded:

$^1$H-NMR (250 MHz, DMSO-d$_6$) δ 2.76 (s, 3H), 6.57 (board s, 1H), 7.46–7.50 (m, 2H), 7.75 (dd, 1H), 8.23–8.29 (m, 2H), 11.56 (broad s, 1H).

ii) Preparation of Title Compound.

N-methylindol-5-carboxylic acid and (1S, 2S)-N-(cis-2-(6-fluoro-2-hydroxy-3-propionylphenyl)-cyclopropyl)-N'-

(5-bromopyrid-2-yl)-urea from Example 10 were condensed using the method described in Example 12 to obtain the title product as the hydrochloride salt.

$^1$H-NMR (250 MHz, CDCl$_3$) δ 1.08 (t, 3H), 1.15–1.25 (m, 1H), 1.39–1.50 (m, 1H), 1.92–2.08 (m, 1H), 2.89 (q, 2H), 2.90 (s, 3H), 3.20–3.35 (m, 1H), 6.55 (broad s, 1H), 6.65 (broad d, 1H), 7.11 (t, 1H), 7.20–7.29 (m, 2H), 7.41 (dd, 1H), 7.72–7.83 (m, 2H), 7.95 (dd, 1H), 8.51 (broad s, 1H), 9.25 (broad s, 1H), 9.43 (broad s, 1H).

EXAMPLE 23

(1S, 2S)-N-[cis-2-(6-fluoro-2-(indol-4-carbonyloxy)-3-propionylphenyl)-cyclopropyl]-N'-(5-bromopyrid-2-yl)-urea Indol-4-carboxylic acid and (1S, 2S)-N-(cis-2-(6-fluoro-2-hydroxy-3-propionylphenyl)-cyclopropyl)-N'-(5-bromopyrid-2-yl)-urea of Example 10 were condensed using the method described in Example 12 to obtain the titled product as the hydrochloride salt.

$^1$H-NMR (250 MHz, CDCl$_3$) δ 1.07 (t, 3H), 1.17–1.30 (m, 1H), 1.31–1.47 (m, 1H), 1.90–2.10 (m, 1H), 2.89 (q, 2H), 3.02–3.18 (m, 1H), 6.75 (broad d, 1H), 7.00–7.35 (m, 4H), 7.55 (dd, 1H), 7.60 (d, 1H), 7.79 (dd, 1H), 7.89 (d, 1H), 8.10 (d, 1H), 9.27 (broad d, 2H).

EXAMPLE 24

(1S, 2S)-N-[cis-2-(6-fluoro-2-(3-amino-4-chlorophenylcarbonyloxy)-3-propionylphenyl)-cyclopropyl]-N'-(5-bromopyrid-2-yl)-urea 3-Amino-4-chlorobenzoic acid and (1S, 2S)-N-(cis-2-(6-fluoro-2-hydroxy-3-propionylphenyl)-cyclopropyl)-N'-(5-bromopyrid-2-yl)-urea of Example 10 were condensed using the method described in Example 12 to obtain the title product as the hydrochloride salt.

$^1$H-NMR (250 MHz, liberated amine, CDCl$_3$) δ 1.10 (t, 3H), 1.17–1.30 (m, 1H), 1.42–1.52 (m, 1H), 1.88–2.01 (m, 1H), 2.88 (q, 2H), 3.19–3.31 (m, 1H), 4.2 (broad s, 2H), 6.80 (broad d, 1H), 7.09 (t, 1H), 7.35 (t, 1H), 7.48–7.60 (m, 2H), 7.66 (d, 1H), 7.73–7.88 (m, 2H), 9.25 (broad s, 2H).

EXAMPLE 25

(1S,2S)-N-[cis-2-(6-fluoro-2-(pyrid-3-ylcarbonyloxy)-3-propionylphenyl)-cyclopropyl]-N'-(5-cyanopyrid-2-yl)-urea

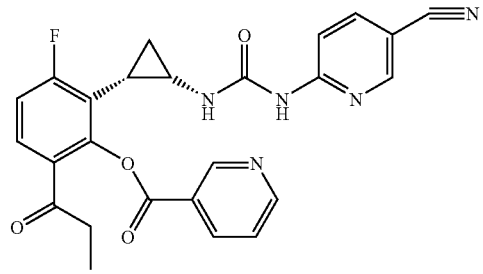

A dried mixture of the compound of Example 8 (50 g, 0.68 mmol), N,N'-dicyclohexylcarbodiimide (0.168 g, 0.81 mmol), nicotinic acid (0.1 g, 0.81 mmol) and 4-(dimethylamino)pyridine (0.041 g, 0.34 mmol) was dissolved in CH$_2$Cl$_2$ (5 ml) and N,N-dimethylformamide (DMF) (2.5 ml). The mixture was then stirred at room temperature. After 20 h. the mixture was filtrated and dried in vacuum, then re-dissolved in a minimum amount of dichloromethane and filtrated. The clear solution was evaporated onto silica and purified by chromatography (ethyl acetate) to give the title compound (0.168 g, 50%). An analytical sample was obtained by re-crystallisation from chloroform-hexane.

$^1$H NMR (CDCl$_3$): 9.89 (br s, 1H), 9.41 (m, 1H), 9.33 (br s, 1H), 8.86 (dd, 1H), 8.46 (dt, 1H), 8.18 (d, 1H), 7.80 (dd, 1H), 7.71 (dd, 1H), 7.49 (ddd, 1H), 7.13 (t, 1H) 6.92 (d, 1H) 3.18 (m, 1H), 2.88 (q, 2H), 1.99 (m, 1H), 1.52 (m, 1H), 1.25 (m, 1H), 1.13 (t, 1.13 (t, 3H).

EXAMPLE 26

(1R,2R)-N-[cis-2-(6-fluoro-2-(pyrid-3-ylcarbonyloxy)-3-propionylphenyl)-cyclopropyl]-N'-(5-cyanopyrid-2-yl)-urea

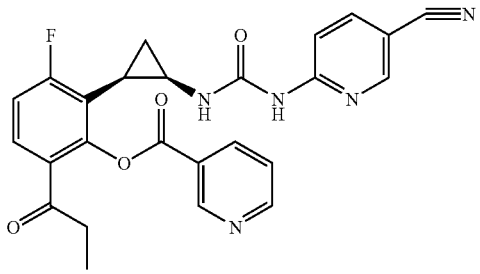

A dried mixture of the compound of Example 6 (0.1 g, 0.27 mmol), N,N'-dicyclohexylcarbodiimide (0.067 g, 0.33 mmol) and nicotinic acid (0.037 g, 0.3 mmol) was suspended in dichloromethane (2 ml). A minimum of DMF was added dropwise to obtain a reasonably clear solution. 4-(dimethylamino)pyridine (0.016 g, 0.14 mmol) was then added. The reaction mixture was stirred in room temperature. After 20 h the solvent was evaporated in vacuum and the crude residue was dissolved in aqueous hydrochloric acid (pH 1–2) and filtrated. The clear solution was then made slightly alkaline with sodium hydrogen carbonate and the precipitated product was filtered of. Purification by chromatography (dichloromethane-methanol, 15:1) gave the title compound 0.072 g (56%).

$^1$H NMR (CDCl$_3$): 9.85 (br s, 1H), 9.42 (s, 1H), 9.35 (br s, 1H), 8.86 (d, 1H), 8.47 (dt, 1H), 8.18 (d, 1H), 7.81 (dd, 1H), 7.71 (dd, 1H), 7.48 (dd, 1H), 7.13 (t, 1H), 6.92 H), 6.92 (d, 1H), 3.19 (m, 1H), 2.91 (q, 2H), 1.99 (m, 1H), 1.49 (m, 1H), 1.24 (m, 1H) 1.13 (t, 3H).

EXAMPLE 27

(1S,2S)-N-[cis-2-(2-(3-(N-ethyl,N-Boc-amino)phenylcarbonyloxy)-6-fluoro-3-propionylphenyl)-cyclopropyl]-N'-(5-cyanopyrid-2-yl)-urea

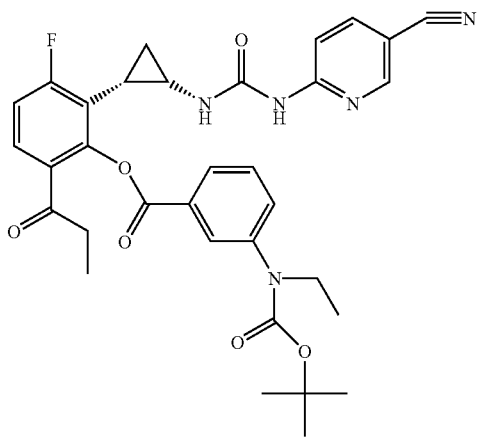

The compound of Example 8 (0.37 g, 1.0 mmol), N,N'-dicyclohexylcarbodiimide (0.25 g, 1.2 mmol), 4-dimethylaminopyridine (0.06 g, 0.5 mmol) and 3-(N-ethyl-N-butoxycarbonyl) aminobenzoic acid (0.320 g, 1.2 mmol) (prepared by reductive amination of 3-aminobenzoic acid, followed by protection of the amino group) were dissolved in dichloromethane (8 ml) and DMF (3 ml). The mixture was then stirred at room temperature. After 18 h. the solvent was removed in vacuum and the crude product was redissolved in dichloromethane and filtered. The clear solution was evaporated onto silica and chromatographed (ethyl acetate-hexane, 3:2) to give sufficiently pure title compound (0.24 g, 39%).

$^1$H NMR (CDCl$_3$): 10.0 (br s, 2H), 8.20 (d, 1H), 8.06 (d, 1H), 8.03 (m, 11H), 7.77 (dd, 1H), 7.70 (dd, 1H), 7.48 (m, 2H), 7.10 (t, 1H), 6.95 (d, 1H), 3.71 (q, 2H), 3.14 (m, 1H), 2.90 (q, 2H), 1.95 (q, 1H), 1.44 (s, 10H), 1.2–1.09 (m, 7H).

EXAMPLE 28

(1S,2S)-N-[cis-2-(2-(3-ethylaminophenylcarbonyloxy)-6-fluoro-3-propionylphenyl)-cyclopropyl]-N'-(5-cyanopyrid-2-yl)-urea

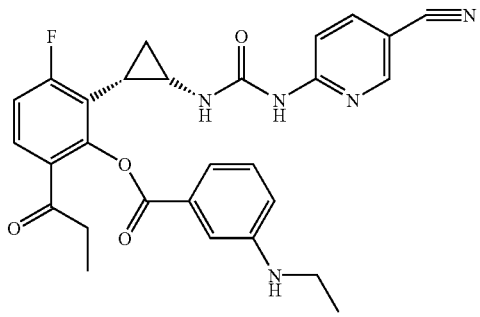

Trifluoroacetic acid (5 ml) was added to a stirred solution of the compound of Example 27 (0.120 mg, 019 mmol) in dichloromethane (10 ml). The mixture was left at room temperature for 1–2 h. then evaporated to dryness. The crude product was purified on HPLC (prep. C-18 column, 40% water in acetonitril) to yield 0.045 g (30%) of the title compound as the trifluoroacetate salt.

$^1$H NMR (CDCl$_3$): 11.08 (br s, 2H), 9.83 (br s, 1H), 9.36 (br s, 1H), 8.23–8.08 (m, 3H), 7.82–7.54 (m, 4H), 7.13 (t, 1H), 7.02 (d, 1H), 3.42 (q, 2H), 3.20 (m, 1H), 2.83 (q, 2H), 1.94 (q, 1H), 1.46 (m, 1H), 1.34 (t, 3H), 1.24 (m, 1H), 1.06 (t, 3H).

EXAMPLE 29

(1S,2S)-N-[cis-2-(2-(3-dimethylaminophenylcarbonyloxy)-6-fluoro-3-propionylphenyl)-cyclopropyl]-N'-(5-cyanopyrid-2-yl)-urea

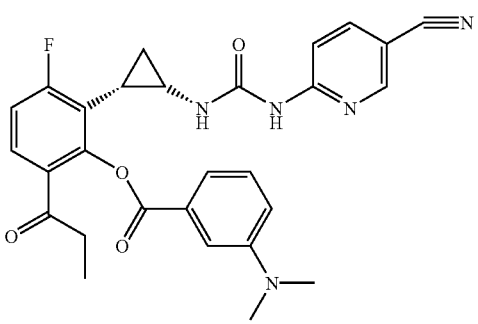

The compound of Example 8 (0.1 g, 0.27 mmol), N,N'-dicyclohexylcarbodiimide (0.067 g, 0.33 mmol), 4-dimethylaminopyridine (0.016 g, 0.14 mmol) and 3-dimethylaminobenzoic acid (0.054 g, 0.39 mmol) were dissolved in dichloromethane (3 ml) and DMF (1 ml). The reaction was left at room temperature for 16 h. The solvent was then removed in vacuum and the solid redissolved in dichloromethane and filtered. Purification by chromatography (ethyl acetate-hexane, 2:1) followed by HPLC (C-18 column, 0.1% TFA in acetonitril) yielded the title compound as the trifluoroacetate salt 0.1 g (58%).

$^1$H NMR (CDCl$_3$): 8.38–8.23 (m, 3H), 7.92–7.69 (m, 4H), 7.15 (t, 1H), 7.05 (m, 1H), 3.32 (s, 6H), 3.26 (m, 1H), 2.89 (q, 2H), 2.02 (m, 1H), 1.55–1.27 (m, 2H), 1.10 (t, 3H).

EXAMPLE 30

(1S,2S)-N-[cis-2-(2-(3-L-valinylaminophenylcarbonyloxy)-6-fluoro-3-propionylphenyl)-cyclopropyl]-N'-(5-cyanopyrid-2-yl)-urea

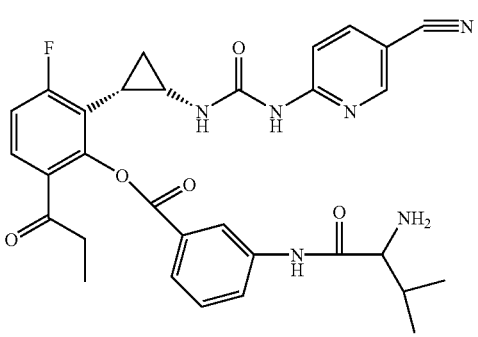

a) 3-(N-Boc-L-valyl)aminomethylbenzoate c) (1S,2S)-N-[cis-2-(2-(3-N-Boc-L-valinylami-nophenylcarbonyloxy)-6 fluoro-3-propionylphenyl)-cyclopropyl]-N'-(5-cyanopyrid-2-yl)-urea

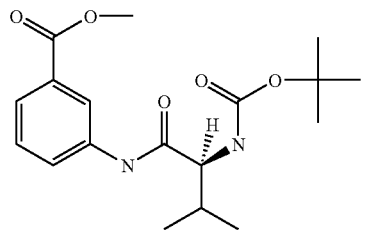

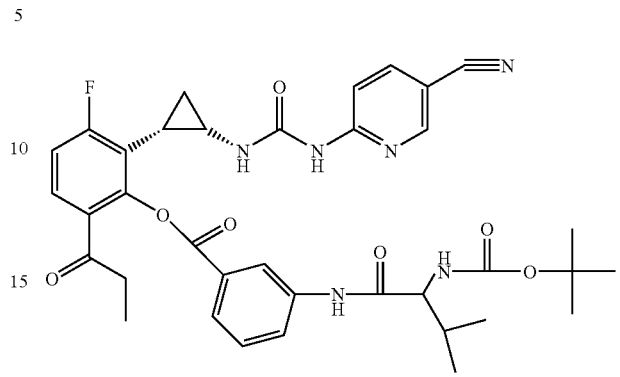

This intermediate is prepared analogously to Villaneuve & Chan, Tetrahedron Letters 1997 vol 37 6489–6492. A mixture of N-tert-butoxycarbonyl-L-valine (2.17 g, 10 mmol) and hexachloroacetone (1.32 g 5 mmol) in dichloromethane (20 ml) was stirred under nitrogen and cooled down to −78 degree C. Triphenylphosphine (2.6 g, 10 mmol) in dichloromethane (10 ml) was added dropwise and the mixture was stirred for 30 min. Methyl 3-aminobensoate (1.5 g, 10 mmol) in dichloromethane (10 ml) was then added dropwise followed by triethylamine (1 g, 10 mmol) in dichloromethane. The reaction was then allowed to reach room temperature after which the solvent was evaporated under vacuum. The residue was purified by silica chromatography (hexane-ethyl acetate, 3:1) followed by recrystallization from ethyl acetate-hexane to give 0.7 g (28%) of the pure intermediate depicted above.

$^1$H NMR (CDCl$_3$): 8.30 (br s, 1H), 8.07 (d, 1H), 7.85–7.75 (m, 2H), 7.37 (t, 1H), 5.15 (d, 1H), 4.05 (m, 1H), 3.91 (s, 3H), 2.26 (m, 1H), 1.48 (s, 9H), 1.03 (dd, 6H).

b) 3-(N-Boc-L-valyl)aminobenzoic acid

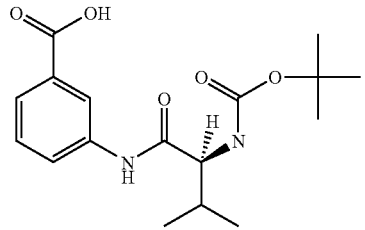

The intermediate of step a) (0.65 mg, 1.8 mmol) was suspended in methanol (6 ml) and water (2 ml). Lithium hydroxide (0.11 g, 3.9 mmol) was added and the mixture was stirred for 24 h. at room temperature. Water (10 ml) was then added and the volume reduced to half. The aqueous solution was washed with 10–20 ml of ethyl acetate then acidified with aqueous hydrochloric acid. Extraction with ethyl acetate (2×20 ml), drying and evaporation in vacuum yielded the pure intermediate depicted above 0.524 g (84%).

$^1$H NMR (CD$_3$OD): 8.23 (t, 1H), 7.84 (d, 1H), 7.76 (d, 1H), 7.42 (t, 1H), 6.70 (m, 1H), 4.00 (m, 1H), 2.08 (m, 1H), 1.45 (a, 9H), 1.00 (d, 6H).

The compound of Example 8 (0.23 g, 0.62 mmol), N,N'-dicyclohexylcarbodiimide (0.153 g, 0.74 mmol), 4-dimethylaminopyridine (0.038 g, 0.3 mmol) and the intermediate of step b) (0.25 g, 0.74 mmol) were dissolved in dichloromethane (9 ml) and DMF (3 ml). The reaction was left at room temperature for 19 h. The solvent was then removed in vacuum and the solid redissolved in dichloromethane and filtered. Purification by chromatography (ethyl acetate-hexane, 1:1) gave 0.029 g (67%) pure N-protected title compound $^1$H NMR (CD$_3$OD): 8.56 (t, 1H), 8.27 (s, 1H), 7.98–7.82 (m, 4H), 7.53 (t, 1H), 7.23 (t, 1H), 7.10 (d, 1H), 3.98 (d, 1H), 3.09 (m, 1H), 2.90 (q, 2H), 2.06–1.93 (m, 2H), 1.44 (m, 10H), 1.18–0.94 (m, 10H).

d) (1S,2S)-N-[cis-2-(2-(3-L-valinylaminophenylcarbonyloxy)-6-fluoro-3-propionylphenyl)-cyclopropyl]-N'-(5-cyanopyrid-2-yl)-urea

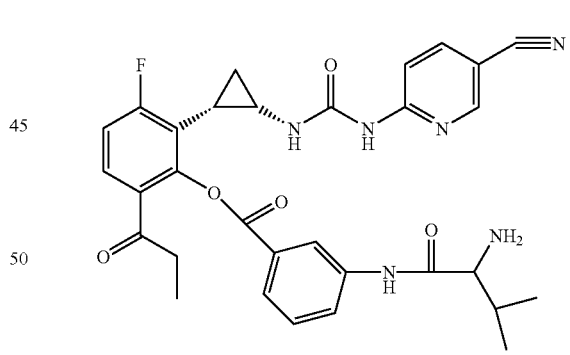

The N-protected compound of step c (0.16 g, 0.23 mmol) and thiophenol (0.054 g, 0.46 mmol) were dissolved in dichloromethane (6 ml) and cooled to 0 degree. Trifluoroacetic acid (6 ml) was added and the mixture was allowed to reach room temperature and left for 1 h. Evaporation to dryness followed by purification by chromatography (dichloromethane-methanol, 10:1.5) gave 0.150 g (90%) of the title compound as the TFA salt.

$^1$H NMR (CD$_3$OD) 8.60 (s, 1H), 8.25 (d, 1H), 8.0–7.85 (m, 4H), 7.53 (t, 1H), 7.21 (t, 1H), 7.09 (d, 1H), 5.0 (m, 1H), 3.12 (m, 1H), 2.96–2.87 (m, 2H), 2.20 (m, 1H), 1.97 (m, 1H), 1.46 (m, 1H), 1.09–1.03 (m, 10H).

EXAMPLE 31

(1S,2S)-N-{cis-2-[6-fluoro-3-propionyl-2-(6-ethylaminopyrid-3-ylcarbonyloxy)phenyl]cyclopropyl}-N'-(5-cyanopyrid-2-yl)urea

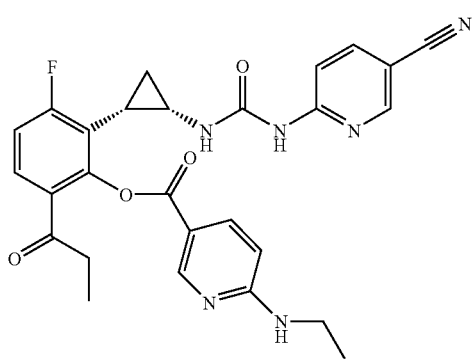

a) 6-ethylaminonicotinic acid

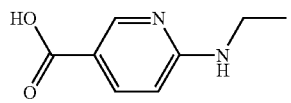

This intermediate is prepared from 6-chloronicotinic acid and ethylamine by the same procedure as described for Example 35 step a). 1-Butanol was substituted for ethyl acetate for the extraction. Recrystallization (MeOH—CHCl$_3$) yielded 0.53 g (50%).

$^1$H NMR (DMSO-d$_6$): 12.1 (br s, 1H), 8.54 (d, 1H), 7.77 (dd, 1H),7.15 (t, 1H), 6.46 (dd, 1H), 3.33 (m, 2H), 1.14 (t, 3H).

b) (1S,2S)-N-{cis-2-F6-fluoro-3-propionyl-2-(6-ethylaminopyrid-3-ylcarbonyloxy)phenyl]cyclopropyl}-N'-(5-cyanopyrid-2-yl)urea

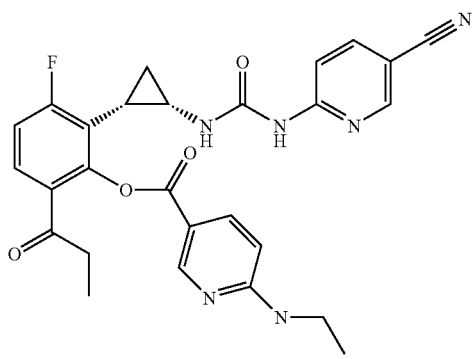

The compound of Example 8 (0.1 g, 0.27 mmol), 6-ethylaminonicotinic acid, (0.084 g, 0.54 mmol), N,N'-dicyclohexylcarbodiimide (0.127 g, 0.62 mmol) and 4-dimethylaminopyridine (0.016 g, 0.13 mmol) were dissolved in DMF (3 ml) and left at ambient temperature. After 19 h. the solvent was removed by vacuum and the residue suspended in dichloromethane and filterated. The solvent was removed and the crude product was purified by chromatography (ethyl acetate-hexane, 2:1) to give the title compound (0.063 g, 45%).

$^1$H NMR (CDCl$_3$): 9.85 (br s, 1H), 9.25 (br s, 1H), 8.91 (d, 1H), 8.18–8.02 (m, 3H), 7.76–7.67 (m, 2H), 7.65 (t, 1H), 6.96 (d, 1H), 6.37 (d, 1H), 5.40 (m, 1H), 3.37 (m, 2H), 3.19 (m, 1H), 2.8 (q, 2H), 1.98 (m, 1H), 1.49 (m, 1H), 1.28 (t, 3H), 1.15 (m, 1H), 1.10 (t, 3H).

EXAMPLE 32

(1S,2S)-N-{cis-2-[6-fluoro-3-propionyl-2-(5-bromopyrid-3-ylcarbonyloxy)phenyl]cyclopropyl}-N'-(5-cyanopyrid-2-yl)urea

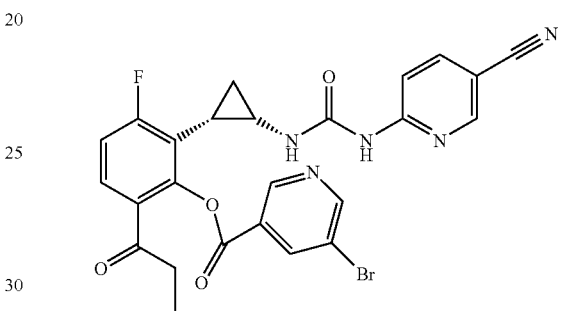

5-Bromonicotinic acid (0.065 g, 0.33 mmol), the compound of Example 8 (0.1 g, 0.27 mmol), N,N'-dicyclohexylcarbodiimide (0.127 g, 0.62 mmol) and 4-dimethylaminopyridine (0.016 g, 0.13 mmol) were dissolved in dichloromethane (4 ml) and left at ambient temperature. After 19 h. the mixture was filtrated and the solvent removed by vacuum. The crude product was purified by chromatography (ethyl acetate-hexane, 1:1) to give the title compound (0.040 g, 27%).

$^1$H NMR (CDCl$_3$): 9.80 (br s,1H), 9.30 (d, 1H), 9.17 (br s, 1H), 8.89 (d, 1H), 8.57 (dd, 1H), 8.57 (dd, 1H), 7.80 (dd, 1H), 7.70 (dd, 1H),7.12 (t, 1H), 6.83 (d, 1H), 3.25 H), 3.25 (m, 1H), 2.87 (q, 2H), 2.00 (q, H), 1.50 (m, 1H), 1.24 (m, 1H), 1.12 (t, 3H).

EXAMPLE 33

(1S,2S)-N-{cis-2-[6-fluoro-3-propionyl-2-(6-aminopyrid-3-ylcarbonyloxy)phenyl]cyclopropyl}-N'-(5-cyanopyrid-2-yl)urea

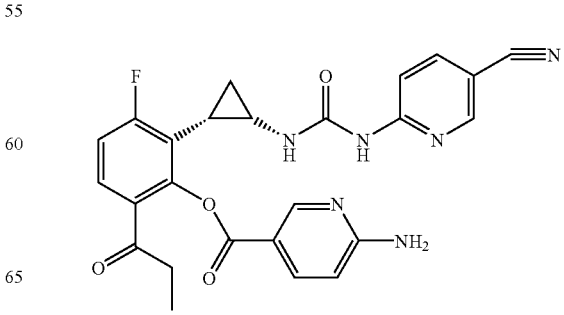

a) 6-aminonicotinic acid, methyl ester

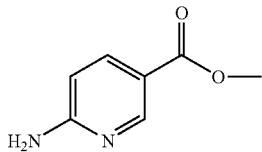

6-Aminonicotinic acid (2 g, 22 mmol) was dissolved in methanol (10 ml) and sulphuric acid (0.5 ml). The solution was refluxed over-night and the solvent was evaporated under vacuum. The crude product was dissolved in water-EtOAc and made alkaline by aqueous sodium hydrogencarbonate. Extraction by EtoAc yielded the pure intermediate depicted above (2.3 g, 70%).

$^1$H NMR (DMSO-$d_6$): 8.51 (dd, 1H), 7.81 (dd, 1H), 6.66 (br s, 2H), 6.45 (dd, 1H) 3.77 (s, 3H).

b) Methyl-6-butoxycarbonylaminonicotinate

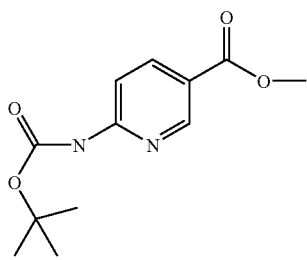

The intermediate of step a) (0.75 g, 4.9 mmol) was dissolved in THF (5 ml). Sodium bis(trimethylsilyl)amide (5 ml, 2 M in THF) was added dropwise. After stirring at room temperature for 30 min. Di-tert-butyldicarbonate (1.1 g, 5 mmol) in THF (8 ml) was added. The reaction mixture was left over-night under nitrogen atmosphere. The solution was then evaporated under vacuum and dissolved in EtOAc (40 ml) and 0.1 M hydrochloric acid (100 ml). The layers were separated and the aqueous phase were extracted twice with EtOAc (40 ml), then made slightly alkaline with aqueous sodium hydrogencarbonate and extracted once again with EtOAc (20 ml). The organic fractions were combined, dried over sodium sulphate and purified by chromatography (EtOAc-hexane, 1:4) to give the pure intermediate depicted above (0.5 g, 40%).

$^1$H NMR (CDCl$_3$): 8.93 (dd, 11H), 8.62 (s, 1H), 8.26 (dd, 1H), 8.06 (dd, 1H), 3.91 (s, 3H), 1.60 (s, 9H).

c) 6-t-butoxycarbonylaminonicotinic acid

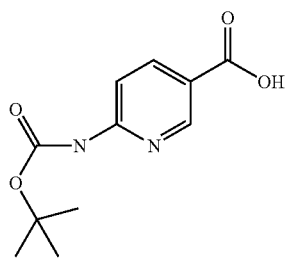

The intermediate of step c) (0.4 g, 1.6 mmol) was suspended in methanol (4 ml) and water (1.25 ml). LiOH (0.1 g, 4 mmol) was added. The slurry was left at room temperature for 48 h. The clear solution was then concentrated under vacuum and dissolved in water and acidified with acetic acid (pH=4–5). Extraction with EtOAc gave the pure intermediate depicted above (0.27 g, 70%). $^1$H.NMR (DMSO-$d_6$): 9.98 (s, 1H), 8.74 (d, 1H), 8.18 (d, 1H), 8.88 (d, 1H), 1.49 (s, (s, 9H).

d) (1S,2S)-N-{cis-2-[6-fluoro-3-propionyl-2-(6-tert-butoxycarbonylamino-pyrid-3-ylcarbonyloxy)phenyl]cyclopropyl}-N'-(5-cyanopyrid-2-yl)urea

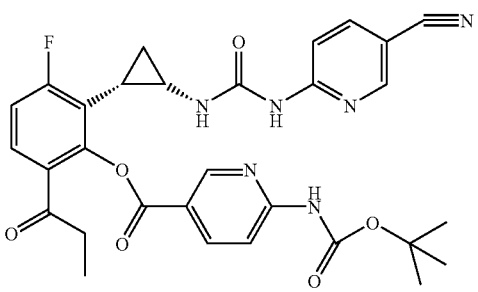

The compound of Example 8 (0.150 g, 0.41 mmol), the intermediate of step c) (0.17 g, 0.49 mmol), N,N'-dicyclohexylcarbodiimide (0.1 g, 0.49 mmol) and 4-dimethylaminopyridine (0.06 g, 0.49 mmol) were dissolved in DMF (2 ml). The mixture was stirred in room temperature overnight, then put in an 50 degree oil bath for 2 h. Evaporation onto silica gel and purification by chromatography yielded the N-protected title compound (0.048 g, 20%).

$^1$H.NMR (CDCl$_3$/CD$_3$OD): 9.02 (s, 1H), 8.43 (dd, 1H), 8.22 (d, 1H), 8.10 (d, 1H), 7.81–7.75 (m, 2H), 7.15 (t, 1H), 7.08 (d, 1H), 3.15–3.05 (m, 1H), 2.90 (q, 2H), 1.96 (m, 1H), 1.56 (s, 9H), 1.50–1.40 (m, 1H), 1.25–1.09 (m, 4H), e) (1S,2S)-N-{cis-2-[6-fluoro-3-propionyl-2-(6-aminopyrid-3-ylcarbonyloxy)phenyl]cyclopropyl}-N'-(5-cyanopyrid-2-yl)urea

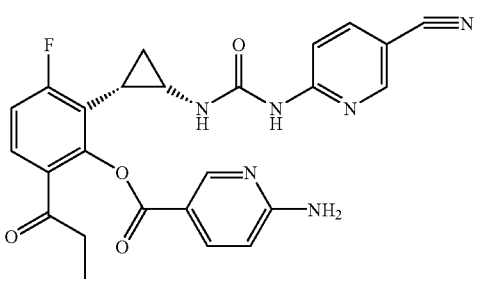

The intermediate of step d) (0.048 g, 0.08 mmol) was dissolved in dichloromethane (2 ml). Trifluoroacetic acid (1 ml) was added and the mixture was stirred for 1 h. Evaporation under vacuum yielded crude title compound. This product was dissolved in ether (2 ml) and left to stand over night. The white precipitates formed were filtrated off to give pure title compound as the trifluoracetate salt (0.032 g, 65%).

¹H.NMR (CD₃OD/CDCl₃): 8.71 (d, 1H), 8.29 (dd, 1H), 8.16 (t, 1H), 8.82.7.74 (m, 2H), 7.20 7.10 (m, 2H), 6.96 (d, 1H), 3.25 (m, 1H), 2.86 (m, 2H), 1.96 (m, 1H), 1.52–1.43 (m, 1H), 1.24–1.19 (m, 1H), 1.09 (t, 3H).

EXAMPLE 34

(1S,2S)-N-{cis-2-[6-fluoro-3-propionyl-2-(6-chloro-pyrid-3-ylcarbonyloxy)phenyl]cyclopropyl}-N'-(5-cyanopyrid-2-yl)urea

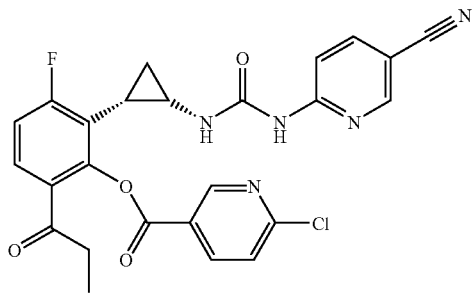

The compound of example 8 (0.15 g, 0.4 mmol), 6-chloronicotinic acid (0.076 g, 0.49 mmol), N,N'-dicyclohexylcarbodiimide (0.1 g, 0.49 mmol) and 4-dimethylaminopyridine (0.024 g, 0.2 mmol) were dissolved in dichloromethane (4 ml). The mixture was left over night. Evaporation under vacuum, purification by chromatography (EtOAc-hexane, 1:2) yielded the title compound (0.067 g, 32%).

¹H.NMR (CDCl₃): 9.77 (br s, 1H), 9.18 (br d, 2H), 8.39 (dd, 1H), 8.14), 7.79 (dd, 1H), 7.71 (dd, 1H), 7.46 (d, 1H), 7.13 (t, 1H), 6.92 (d, 1H), 3.25 (m, 1H), 2.88 (q, 2H), 2.00–1.90 (m, 1H), 1.55–1.46 (m, 1H), 1.25–1.22 (m, 1H), 1.11 (t, 3H)

EXAMPLE 35

(1S,2S)-N-{cis-2-[6-fluoro-3-propionyl-2-(6-dimethylaminopyrid-3-ylcarbonyloxy)phenyl]cyclopropyl}-N'-(5-cyanopyrid-2-yl)urea

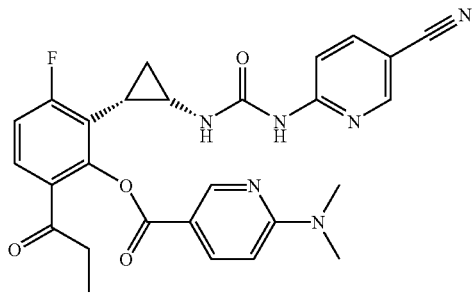

a) 6-dimethylaminonicotinic acid

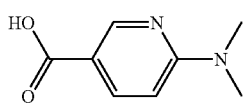

6-Chloronicotinic acid (0.5 g, 3.17 mmol) and dimethyl amine 10 ml, 40% in water) were heated in a sealed pressure vessel at 130° C. for 6 h. The solvent was then removed and the residue was taken up in water and the pH was adjusted to 4–5. Extraction with dichloromethane yielded the pure intermediate depicted above (0.1 g, 20%).

¹H.NMR (CDCl₃): 8.87 (dd, 1H), 8.04 (dd, 1H), 6.49 (dd, 1H), 3.18 (s, 6H).

b) (1S,2S)-N-{cis-2-[6-fluoro-3-propionyl-2-(6-dimethylaminopyrid-3-ylcarbonyloxy)phenyl]cyclopropyl}-N'-(5-cyanopyrid-2-yl)urea The compound of Example 8 (0.13 g, 0.3 mmol), the intermediate of step a) (0.05 g, 0.3 mmol), N,N'-dicyclohexylcarbodiimide (0.09 g, 0.4 mmol) and 4-dimethylaminopyridine (0.02 g, 0.18 mmol) were dissolved in dichloromethane (3 ml) and DMF (1 ml). The mixture was left overnight. Evaporation under vacuum and purification by chromatography (EtOAc-hexane, 2:1) yielded the title compound (0.06 g, 39%).

¹H.NMR (CDCl₃): 10.10 (br s, 1H), 9.29 (br s, 1H), 8.18 (d, 1H), 8.12 (dd, 1H), 7.76–7.60 (m, 2H), 7.06 (t, 1H), 6.95 (d, 1H), 6.62 (d, 1H), 3.18 (m, 7H), 2.83 (q, 2H), 2H), 2.10–1.99 (m, 1H), 1.51–1.42 (m, 1H), 1.19 (m, 1H), 1.09 (t, 3H).

EXAMPLE 36

(1S,2S)-N-[cis-2-(6-fluoro-2-O-3-propionylphenyl)-cyclopropyl]-N'-(5-cyanopyrid-2-yl) urea-O-4-hydroxybenzoate a) 4-benzyloxybenzoic acid.

To a solution of 4-hydroxybenzoic acid (60.9 g, 50 mmole) in 150 ml DMF was added potassium tert.-butoxide (12.34 g, 110 mmole) and the mixture was stirred at room temperature for one hour. Benzyl bromide (20.5 g, 120 mmole) was added and the mixture was stirred for two days at room temperature. The mixture was evaporated under reduced pressure and 100 ml 1,4-dioxane and a solution of sodium hydroxide (6.0 g, 150 mmole)in 50 ml water was added. The mixture was refluxed for two hours, cooled and evaporated under reduced pressure. Water was added and the mixture was acidified with acetic acid. The product was filtered, washed with cold water and dried. Yield: 10.2 g=89%.

b) 4-benzyloxybenzoyl Chloride.

To a mixture of 4-benzyloxybenzoic acid (2.28 g, 10 mmole) in 20 ml dried dichloromethane were added five drops of DMF and 2.5 ml thionyl chloride. The mixture was refluxed for three hours and evaporated under reduced pressure. Yield: 2.45 g=100% c) (1S, 2H)-N-[cis-2-(6-fluoro-2-O-3-propionylphenyl)cyclopropyl]-N'-[2-(5-cyanopyrid-2-yl) urea O-4-benzyloxybenzoate.

To a solution of (1S, 2S)-N-[cis-2-(6-fluoro-2-hydroxy-3-propionylphenyl) cyclopropyl]-N'-(5-cyanopyrid-2-yl) urea (184 mg, 0.5 mmole) in 3 ml DMF was added potassium tert. butoxide (78.5 mg, 0.7 mmole) and the mixture was stirred for one hour at room temperature. A solution of 4-benzyloxybenzoylchloride (185 mg, 0.75 mmole) in 1 ml DMF was added and the mixture was stirred overnight at room temperature. 40 ml ethyl acetate were added and the organic phase was washed four times with water. The solution was dried with sodium sulfate and evaporated under reduced pressure. The product was isolated by silica gel column chromatography. Yield: 180 mg=62%.

$^1$H-NMR (DMSO δ-6) 0.92 (m, 4H) 1.31(m, 1H) 1.85 (m, 1H) 2.82 (m, 2H) 3.06 (m, 1H) 5.26 (s, 2H) 7.20 (m 2H) 7.38–8.12 (m, 1H) 8.38 (m, 1H)

d) Synthesis of (1S, 2S)-N-[cis-2-(6-fluoro-2-O-3-propionylphenyl) cyclopropyl]-N'-(5-cyanopyrid-2-yl)]urea-O-4-hydroxybenzoate A solution of (1S, 2S)-N-[cis-2-(6-fluoro-2-O-3-propionylphenyl)cyclopropyl]-N'-(5-cyanopyrid-2-yl)urea-O-4-benzyloxybenzoate (170 mg, 0.29 mmole) in 15 ml ethyl acetate and 15 ml methanol was hydrogenated with 10% palladium on charcoal (30 mg) three times at room temperature and normal pressure. The catalyst was filtered and washed with ethyl acetate and methanol and the solution was evaporated under reduced pressure. The product was isolated by silica gel column chromatography. Yield: 100 mg=70%.

$^1$H-NMR (DMSO δ-6) 0.93 (m, 4H) 1.32 (m, 1H) 1.88 (m,1H) 2.85 (m, 2H) 3.05 (m, 1H) 6.92 (m, 2H) 7.38 (m, 2H) 8.00 (m, 4H) 8.38 (m, 1H)

EXAMPLE 37

(1S, 2S)-N-[cis-2-(6-fluoro-2-O-3-propionylphenyl)-cyclopropyl]-N'-[2-(5-cyanopyridyl)]urea-O-methylene-4-hydroxybenzoate a) Methyl-4-(4-methoxybenzyloxy)Benzoate.

To a solution of methyl 4-hydoxybenzoate (6.85 g, 45 mmole) in 80 ml DMF was added potassium tert. butoxide (5.6 g, 51 mmole) and the mixture was stirred at room temperature for one hour. 4-Methoxybenzyl chloride (8.3 g, 52 mmole) was added and the mixture was stirred overnight at room temperature. The mixture was evaporated under reduced pressure and 200 ml ethyl acetate was added. The organic phase was washed four times with water, dried with sodium sulfate and evaporated under reduced pressure. Yield: 12.3 g=100%

$^1$H-NMR (CDCl$_3$) 3.82 (s, 3H) 3.88 (s, 3H) 5.03 (s, 2H) 6.96 (m, 4H) 7.36 (d, 2H) 7.98 (d, 2H)

b) 4-(4-methoxybenzyloxy)benzoic acid

To a solution of methyl 4-(4-methoxybenzyloxy) benzoate (12.2 g, 44.8 mmole) in 50 ml 1,4-dioxane was added a solution of lithium hydroxide (2.15 g, 89,6 mmole) and the mixture was stirred overnight at 60° C. The mixture was evaporated under reduced pressure and 5% acetic acid was added. The product was filtered, washed with water and dried. Yield: 10.1 g=87%

$^1$H-NMR (DMSO δ-6) 3.74 (s, 3H) 5.08 (s, 2H) 6.92 (d, 2H) 7.06 (d, 2H) 7.36 (d, 2H) 7.90 (d, 2H)

c) Chloromethyl 4-(4-methoxybenzyloxy)benzoate

To a solution of 4-(4-methoxybenzyloxy) benzoic acid (5.16 g, 20 mmole) in 100 ml 1,4-dioxane was added a 40% solution of tetrabutylammonium hydroxide (14.27 g, 22 mmole) and the mixture was stirred 2 hours at room temperature. The mixture was evaporated under reduced pressure and co-evaporated two times with 1,4-dioxane and two times with toluene. The dried product was dissolved in 60 ml dichloromethane and iodochloromethane (35.3 g 200 mmole) was added. The solution was stirred for two days at room temperature and evaporated under reduced pressure. About 100 ml ethyl actate was added and the organic phase washed twice with water, dried with sodium sulfate and evaporated under reduced pressure. The product was isolated by silica gel column chromatography.Yield: 4.48 g=73%

$^1$H-NMR (CDCl$_3$) 3.83 (s, 3H) 5.06 (s, 2H) 5.94 (s, 2H) 7.00 (m, 4H) 7.36 (d, 2H) 8.05 (d, 2H)

d) Iodomethyl-4-(4-methoxybenzyloxy) benzoate

To a solution of chloromethyl-4-(4-methoxybenzyloxy) benzoate (0.77 g, 2.5 mmole) in 15 ml dry acetone was added sodium iodide (1.87 g, 12.5 mmole) and the mixture was stirred overnight at room temperature. The mixture was evaporated under reduced pressure and extracted with ethyl actate/water. The organic phase was washed with a 5% sodium thiosulfate solution, dried with sodium sulfate and evaporated under reduced pressure. Yield 0.86 g=86%

$^1$H-NMR (CDCl$_3$) 3.84 (s, 3H) 5.05 (s, 2H) 6.14 (s, 2H) 6.98 (m, 4H) 7.36 (d, 2H) 8.00 (d, 2H)

e) (1S, 2S)-N-[cis-2-(6-fluoro-2-O-3-propionylphenyl (cyclopropyl]-N'-[2-(5-cyanopyridyl)urea-O-methylene-4-(4-methoxybenzyloxy) benzoate To a solution of (1S, 2S)-N-[cis-2-(6-fluoro-2-hydroxy-3-propionylphenyl) cyclopropyl]-N'-[2-(5-cyanopyridyl)] urea (368 mg, 1 mmole) in 5 ml DMF was added a suspension of 60% sodium hydride in mineral oil (44 mg, 1.1 mmole) and the mixture was stirred for one hour at room temperature. A solution of iodomethyl-4-(4-methoxybenzyloxy) benzoate (0.84 g, 2.1 mmole) in 2 ml THF was added and the mixture was stirred overnight at room temperature. 50 ml ethyl acetate were added and the organic phase was washed four times with water, dried with sodium sulfate and evaporated under reduced pressure. The product was isolated by silica gel column chromatography. Yield: 525 mg=82%

$^1$H-NMR (CDCl$_3$) 0.91 (m, 3H) 1.32 (m, 1H) 1.60 (m, 1H) 2.04 (m, 1H) 2.90 (m, 2H) 3.20 (m, 1H) 3.82 (s, 3H) 5.04 (s, 2H) 5.84–6.06 (m, 2H) 6.91–8.18 (m,13H)

f) (1S, 2S)-N-[cis-2-(6-fluoro-2-O-3-propionylphenyl)cyclopropyl]-N'-[2-(5-cyanopyridyl)]urea-O-methylene-4-hydroxybenzoate To a solution of (1S, 2S)-N-[cis-2-(6-fluoro-2-O-3-propionylphenyl)cyclopropyl]N'-[2-(5-cyanopyridyl)urea-O-methylene-4-(4-methoxybenzyloxy) benzoate (100 mg, 0.156 mmole) in 4 ml dichloromethane was added TFA (0.5 ml) and the solution was stirred for one hour at room temperature. The solution was evaporated under reduced pressure and the product was isolated by silica gel column chromatography. Yield: 45 mg=55%

$^1$H-NMR (DMSO δ-6) 0.84 (m, 3H) 1.10 (m, 1H) 1.48 (m, 1H) 2.12 (m, 1H) 2.80 (m, 2H) 3.19 (m, 1H) 5.85–6.02 (m, 2H) 6.84 (m, 2H) 7.18 (m, 1H) 7.46 (m, 2H) 7.74 (m, 2H) 8.04 (m, 2H) 8.38 (m, 1H)

EXAMPLE 39

(1S,2 S)-N-{cis-2-[6-fluoro-3-propionyl-2-(6-methy-laminopyrid-3-ylcarbonyloxy)phenyl]cyclopropyl}-N'-(5-cyanopyrid-2-yl)urea

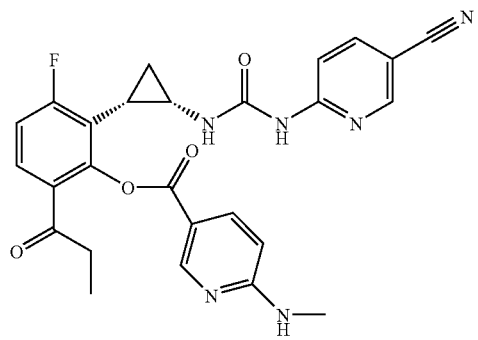

This compound was prepared from 6-methylaminonicotinic acid 0.050 g, 0.33 mmol) and the compound of Example 8 (0.1 g, 0.27 mmol) by the same procedure as for Example 31. The crude product (containing the title compound and unreacted starting material) was purified by chromatography (ethyl acetate) to give 0.030 g (22%) of the title compound.

$^1$H.NMR (CDCl$_3$): 9.8 (br s, 1H), 9.25 (br s, 1H), 8.90 (d, 1H), 8.20 (d, 1H), 8.10 (m, 1H), 7.72 (m, 2H), 7.08 (t, 1H), 6.9 (d, 1H), 6.37 (d, 1H), 3.20 (m, 1H), 2.95 (d, 3H), 2.85 (q, 2H), 1.95 (m, 1H), 1.48 (m, 1H), 1.10 (t, 3H).

BIOLOGICAL EXAMPLE 1

Resistance Pattern

Compounds of the invention were tested for antiviral activity against a number of HIV strains, including wild type and known mutants arising from the use of other non-nucleoside reverse transcriptase inhibitors as described in the review of Schinazi at al, International Antiviral News, vol 4 no 6, pp 95–107 (1996). Results are presented in Table 1.

TABLE 1

| HIV strain | Example 5 | Example 6 | Example 8 | Prior art* |
|---|---|---|---|---|
| wild type | 0.0012 | 0.0008 | 0.0007 | 0.0056 |
|  | +/− 0.0004 | +/− 0.0004 | +/− 0.0002 | +/− 0.004 |
| wild type | 0.01 | 0.006 | 0.007 | 0.023 |
| 50% serum | +/− 0.009 | +/− 0.003 | +/− 0.001 | +/− 0.011 |
| K103N | 0.05 | 0.017 | 0.037 | 0.13 |
|  | +/− 0.04 | +/− 0.008 | +/− 0.007 | +/− 0.060 |
| K103N | 0.38 | 0.17 | 0.39 | 0.9 |
| 50% serum | +/− 0.31 | +/− 0.07 | +/− 0.31 | +/− 0.6 |
| Y181C | 0.017 | 0.006 | 0.006 | 0.13 |
|  | +/− 0.018 | +/− 0.002 | +/− 0.001 | +/− 0.02 |
| Y181C | 0.10 | 0.08 | 0.08 | 0.13 |
| 50% serum | +/− 0.06 | +/− 0.05 | +/− 0.06 | +/− 0.07 |
| Y188L | 0.13 | 0.08 | 0.06 | 0.17 |
|  | +/− 0.07 | +/− 0.06 | +/− 0.02 | +/− 0.03 |
| Y188L | 1.5 | 0.9 | 1.0 | 1.9 |
| 50% serum | +/− 0.9 | +/− 0.05 | +/− 0.05 | +/− 1.5 |
| L100I, Y181C | ND | ND | 0.34 | 1.0 |
|  |  |  | +/− 0.06 |  |
| L100I | ND | ND | 0.009 | 0.026 |
|  |  |  | +/− 0.001 | +/− 0.009 |
| SI | >41 600 | 22 500 | 87 000 | 5 900 |
| SI | ND | 8 830 | 4 285 | 800 |
| 50% serum |  |  |  |  |

The assay included multiple determinations with XTT in MT-4 cells (Weislow et al, J Nat Cancer Inst 1989, vol 81 no 8, 577 et seq) including determinations in the presence of 50% human serum to indicate the contribution of protein binding. The ED$_{50}$ is presented in µg/ml. The initial data on the calculated therapeutic index (SI) are also presented, defined as the dose producing 50% toxicity in the corresponding HIV-free cells divided by the ED$_{50}$. The prior art compound, from the 1995 ICAR Santa Fe is depicted above.

It will be apparent that the compounds of the invention, especially the enantiomers, have ED$_{50}$ values which are distinctly lower than hitherto known compounds, including the values against the known problematic mutants K103N and Y181C, as well as L100I and the double mutant L100I, Y181C. Furthermore the therapeutic indices for the enantiomers are 5 to 10 fold greater than the prior art compound. These results should be seen in the context of HIV therapy where patients can expect to take medication for many years, if not for the rest of their lives against the notoriously resistance prone virus HIV. Thus a large SI is needed to avoid cumulative toxicity, while at the same time allowing adequate dosing to maintain therapeutic pressure and prevent the spontaneous generation of multiply resistant HIV strains.

BIOLOGICAL EXAMPLE 2

Time to Resistance

2×10$^4$ MT4 cells per well in a microtitre plate are infected with 5–10 TCID$_{50}$ of HIV-1 $_{IIIB}$. The compounds being tested are added at concentrations around ED$_{50}$ using 8 duplicates per concentration. After 6 days of incubation the RT activity in 10 µl supernatent is measured.

The following procedure is followed at subsequent passages of the cultures once per week.: Virus produced at the concentration of test compound showing >50% of the RT activity of untreated infected cells (SIC, Starting Inhibitory Concentration) are passaged to fresh MT4 cells. 15 µl supernatent from each of the eight duplicates are transferred to cells without the test compound (control) and to cells with test compound at the same concentration, and additionally two respectively fivefold higher concentrations. (See Table 2 below)

When viral growth is permitted at the highest non-toxic concentration (5–40 µM), 2–4 parallel wells are collected and expanded to give material for sequence analysis and cross-wise resistance.

TABLE 2

| | | Viral growth permitted Virus production inhibited | | | |
|---|---|---|---|---|---|
| | | | | | 125 × SIC |
| | | | | 125 × SIC | 25 × SIC → |
| | | | 25 × SIC | 25 × SIC | 5 × SIC |
| | | 25 × SIC | 5 × SIC → | 5 × SIC → | No |
| | 25 × SIC | 5 × SIC → | 5 × SIC | No compound | compound |
| | 5 × SIC | SIC | | | |
| | SIC → | No compound | | | |
| SIC → | No compound | | | | |
| Pass 1 | Pass 2 | Pass 3 | Pass 4 | Pass 5 | |

FIG. 1 plots the growth of viral resistance for a compound of the invention (Example 8) against time. Also plotted is the corresponding curve for the closest Santa Fe compound, mentioned above. It will be apparent that the compounds of the invention show a significantly slower rate of resistance development.

BIOLOGICAL EXAMPLE 3

P450 Metabolism

The metabolism of compounds of the invention through the main isoforms of the human cytochrome system P450 were determined in baculovirus infected insect cells transfected with human cytochrome P450 cDNA (supersomes) (Gentest Corp., Woburn USA).

The test compounds at concentrations 0.5, 5 and 50 μM were incubated in duplicate in the presence of supersomes overexpressing various cytochrome P450 isoforms, including CYP1A2+P450 reductase, CYP2A6+P450 reductase, CYP2C9-Arg 144+P450 reductase, CYP2C19+P450 reductase, CYP2D6-Val 374+P450 reductase and CYP3A4+P 450 reductase. Incubates contain a fixed concentration of cytochrome P450 (eg 50 pmoles) and are conducted over 1 hour. The involvement of a given isoform in the metabolism of the test compound is determined by UV HPLC chromatographically measuring the disappearance of parent compound.

After testing the three concentrations for 7.5 minutes, the %-age remaining figures suggest that CYP3A4, 1A2, 2C19 and 2A6 are involved in the metabolism of the compound of Example 7. Similar constellations of P450 isoforms are also involved in the metabolism of the prior art Santa Fe halopyridinyl compounds.

Surprisingly, no significant p450 metabolism with any isomer was registered for the compound of Example 8, implying that the compound is stable in vivo and that the possibility of disturbance of the metabolism of coadministered drugs is correspondingly low.

BIOLOGICAL EXAMPLE 4

Pharmacokinetics

The release of a compound of Formula I from an orally administered prodrug of Formula II was monitored in rats. The compound of Example 7 was made up in a propylene glycol vehicle and orally administered to paired fasted male Sprague Dawley rats at a dose corresponding to 0.027 mmol/kg. At the indicated time intervals, 0.2 ml blood was collected from a catheter implanted in the canis jugularis, centrifuged and frozen for later analysis. The released drug of Formula I (Example 6) was assayed by HPLC. Aliquots comprising 40–100 μl of each plasma sample are mixed with an equal volume of acetonitrile (10 seconds, Vibrofex). The sample is centrifuged (2 min, 14000 RPM) and 30 μl of the supernatant is injected into an HPLC system, as follows.

| Pre column: | RP-18, 7 μm, 15 × 3.2 mm |
|---|---|
| Column: | YMC basic, 3 μm, 150 × 3 mm |
| Mobile phase: | 60% acetonitrile in 3 mM ammonium acetate, pH 6.4 |
| Flow rate: | 0.4 ml/min |
| Detection: | UV, 250 nm |

TABLE 3

| time (min) | plasma level of mother compound (μg/ml) |
|---|---|
| 30 | 0.24, 0.35 |
| 60 | 0.18, 0.28 |
| 120 | 0.13, 0.17 |
| 240 | 0.07, 0.12 |
| 360 | 0.05, 0.07 |

In Table 3 it is clear that oral administration of the prodrugs of Formula II releases in vivo clinically significant amounts of the compounds of Formula I.

BIOLOGICAL EXAMPLES 5–8 i) Preparatory

The rats used in pharmacokinetic examples were male Sprague-Dawley, with a weight about 200–250 g. The rats were fasted for at least 16 hours before the experiment, but had free access to water. The day before the experiment the rats were anaesthetized using a mixture of Efrane®, laughing gas and oxygen. A catheter was introduced into the vena jugularis. On the day of the experiment the weights of the rats were noted. The animals were shortly anaesthesized before the oral dose was given or the iv dose injected into the back of the neck. Each substance was administered to duplicate rats.

Monkeys were fasted for 12 hours prior to oral administration but had free access to water. The test compound was delivered via an infant nasogastric feeding tube. After 6 hours the monkeys received an apple.

ii) Dose Preparation

Appropriate quantities of the active ingredients described in the following examples were dissolved/suspended in a solution of propylene glycol or 10% Acacia and 1% of Tween in water for oral administration. Compounds were dissolved in DMSO for intravenous administration.

iii) Blood Sampling

Blood samples (typically 0.6 ml for rats, 2 ml for monkeys) were taken before and at the indicated time intervals, as plotted, after drug administration. Monkeys were tapped from the femoral vein into EDTA-containing tubes. The blood samples were centrifuged infectious agents neutralised with 1% SDS/64°/20 min and plasma stored at −20° C.

iv) Bioanalysis

Plasma samples are prepared as follows: 40–100 μl of plasma is mixed with an equal volume of acetonitrile (10 seconds, Vibrofex). The sample is centrifuged (2 min, 14000 RPM) and 30 μl of the supernatant is injected into an HPLC system, as follows.

| Pre column: | RP-18, 7 μm, 15 × 3.2 mm |
|---|---|
| Column: | YMC basic, 3 μm, 150 × 3 mm |
| Mobile phase: | 60% acetonitrile in 3 mM ammonium acetate, pH 6.4 |
| Flow rate: | 0.4 ml/min |
| Detection: | UV, 250 nm |

BIOLOGICAL EXAMPLE 5

Comparison with the closest prior art compound

Figure 2:
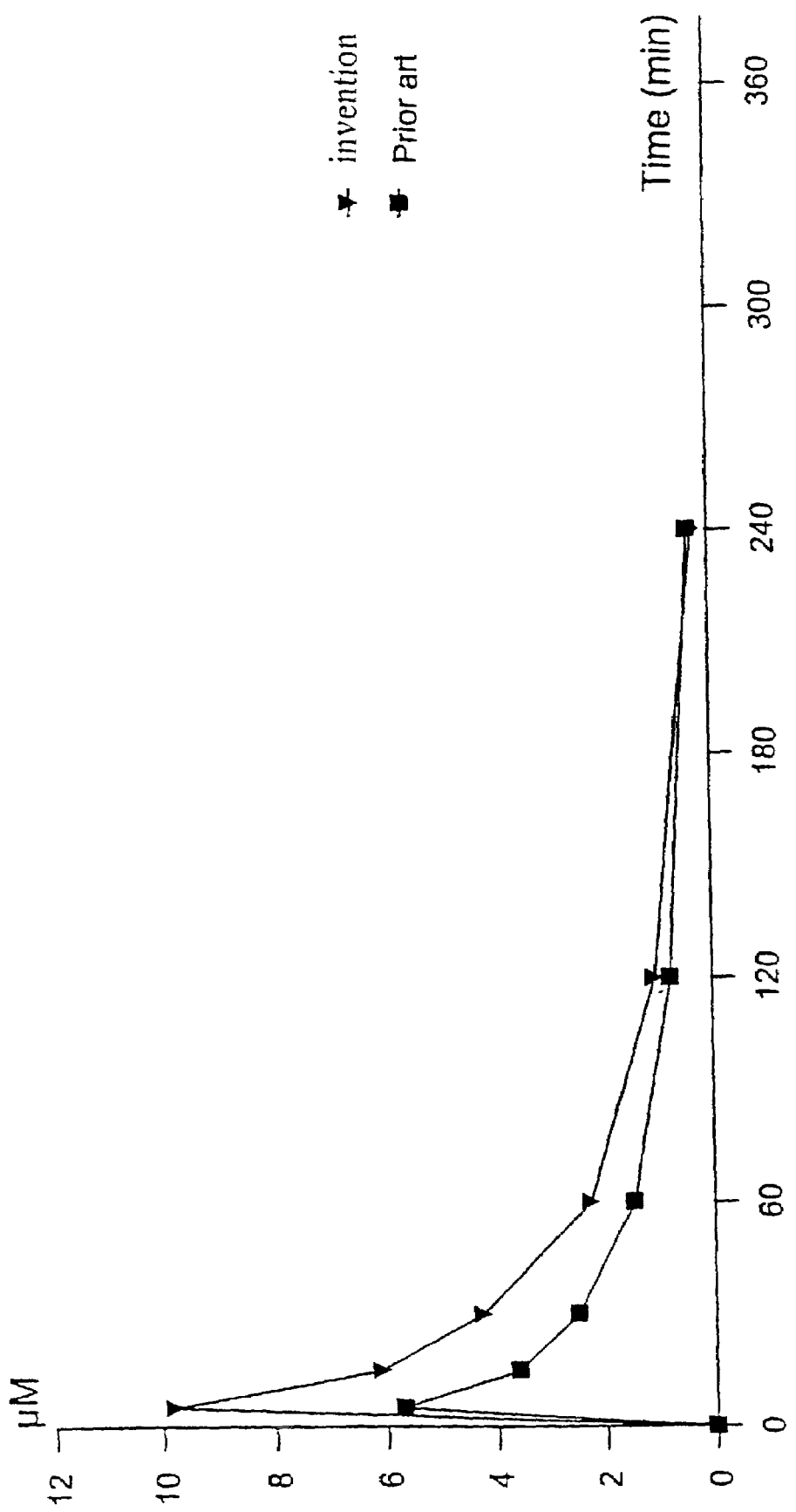
FIG. 2 depicts time vs plasma levels after oral administration to rats of a compound of the invention or a prior art compound, as described in Biological Example 5.

The in vivo stability and availability of the compounds of Formula I were compared with the closest Santa Fe compound, namely (+/−)—N-(cis-2-(6-fluoro-2-hydroxy-3-propionylphenyl)-cyclopropyl)-N'-(5-chloropyridyl-2-yl)-urea, whereby 0.024 mmol/kg doses of the respective compounds were administered in a DMSO vehicle. FIG. 2 is a plot of plasma levels of the respective compounds (n=2 in each case) over time. It will be apparent that the respective curves follow a common pattern but that the compound of the invention has an AUC (0–4 h) in excess of 1.5 times the AUC (0–4 h) of the closest prior art compound. In other words the compounds of the invention provide a 50% greater in vivo exposure than the previously described derivative, although although whether this is due to a slower clearance of the compounds of the invention or a greater degree of tissue binding with the prior art compounds, etc has yet to be determined.

BIOLOGICAL EXAMPLE 6

Bioequivalence of Prodrugs and Mother Compound

Various compounds of Formula II (that is prodrugs of the compounds of Formula I) were administered to rats and the plasma levels of the mother compound of the invention (in this example the compound of Example 10) were monitored over time. The vehicle was 10% acacia and 1% Tween in water or propylene glycol (asterisked). Plasma level figures in Table 4 refer to individual animals.

TABLE 4

| Compound | Dose (mmol/kg) | Time (min) | plasma level of mother compound (μg/ml) | | | |
|---|---|---|---|---|---|---|
| Example 12 | 0.053 | 30 | 0.2 | 0.3 | 0.06 | 0.11 |
| | | 60 | 0.2 | 0.4 | 0.12 | 0.20 |
| | | 90 | 0.3 | 0.4 | | |
| | | 120 | 0.2 | 0.5 | 0.10 | 0.20 |
| | | 180 | 0.3 | 0.4 | 0.11 | 0.23 |
| | | 240 | 0.3 | 0.4 | 0.08 | 0.24 |
| | | 330 | | | 0.08 | 0.15 |
| | | 420 | | | 0.05 | 0.12 |
| Example 12 | 0.026 | 30 | 0.09 | 0.05 | | |
| | | 60 | 0.10 | 0.07 | | |
| | | 120 | 0.09 | 0.08 | | |
| | | 180 | 0.08 | 0.08 | | |
| | | 240 | 0.06 | 0.05 | | |
| | | 330 | | 0.03 | | |
| | | 420 | | 0.02 | | |
| Example 22 | 0.026 | 30 | | 0.08 | | |
| | | 60 | 0.05 | 0.11 | | |
| | | 120 | 0.04 | 0.08 | | |
| | | 180 | 0.03 | 0.07 | | |
| | | 240 | 0.02 | 0.04 | | |
| | | 360 | <0.02 | <0.02 | | |
| Example 14 | 0.053 | 30 | 0.10 | 0.08 | | |
| | | 60 | 0.15 | 0.08 | | |
| | | 120 | 0.27 | 0.07 | | |
| | | 180 | 0.35 | 0.09 | | |
| | | 240 | 0.35 | 0.09 | | |
| | | 360 | 0.24 | 0.12 | | |
| Example 18 | 0.053 | 30 | 0.12 | 0.03 | | |
| | | 60 | 0.15 | 0.03 | | |
| | | 120 | 0.15 | 0.07 | | |
| | | 180 | 0.23 | 0.14 | | |
| | | 240 | 0.12 | 0.16 | | |
| | | 360 | 0.08 | 0.08 | | |

TABLE 4-continued

| Compound | Dose (mmol/kg) | Time (min) | plasma level of mother compound (μg/ml) | |
|---|---|---|---|---|
| Example 23 | 0.053 | 30 | 0.14 | 0.32 |
| | | 60 | 0.22 | 0.49 |
| | | 120 | 0.36 | 0.49 |
| | | 180 | 0.44 | 0.32 |
| | | 240 | 0.35 | 0.27 |
| | | 360 | 0.14 | 0.14 |
| Example 17 | 0.053 | 30 | 0.05 | 0.05 |
| | | 60 | 0.07 | 0.05 |
| | | 120 | 0.06 | 0.14 |
| | | 180 | 0.07 | 0.20 |
| | | 240 | 0.07 | 0.17 |
| | | 360 | 0.04 | 0.12 |
| Example 29 | 0.027* | 30 | 0.258 | 0.031 |
| | | 60 | 0.268 | <0.03 |
| | | 120 | 0.128 | <0.03 |
| | | 240 | 0.051 | <0.03 |
| | | 360 | <0.03 | <0.03 |
| Example 37 | 0.027* | 30 | 0.234 | 0.137 |
| | | 60 | 0.273 | 0.189 |
| | | 120 | 0.111 | 0.133 |
| | | 240 | 0.056 | 0.045 |
| | | 360 | 0.054 | 0.056 |

It will be apparent that the prodrugs of Formula II release in vivo clinically relevant amounts of the compounds of Formula I into the plasma. The absolute oral bioavailability (determined relative to the iv dose, as decribed in the preparatory section) was 28–33% for the compound of Example 37 and 27% for the evaluable animal with the compound of Example 27.

BIOLOGICAL EXAMPLE 7

Bioavailability in Different Species

A prodrug of the invention of Formula II (Example 12) was administered at the same dose (0.026 mmol/kg) and in the same vehicle (10% acacia and 1% Tween in water) to rats and cynomolgus monkeys. Plasma levels of the mother compound of Formula I (Example 10) was measured as a function of time.

TABLE 5

| species | time (min) | plasma level of mother compound (μg/ml) | |
|---|---|---|---|
| rat | 30 | 0.09 | 0.05 |
| | 60 | 0.10 | 0.07 |
| | 120 | 0.09 | 0.08 |
| | 180 | 0.08 | 0.08 |
| | 240 | 0.06 | 0.05 |
| | 330 | | |
| | 420 | | |
| monkey | 45 | 0.08 | 0.04 |
| | 90 | 0.20 | 0.26 |
| | 180 | 1.0 | 0.55 |
| | 240 | 0.72 | 0.54 |
| | 360 | 0.38 | 0.39 |
| | 600 | 0.13 | 0.10 |
| | 24 h | 0.03 | 0.03 |

It will be apparent that the prodrugs of Formula II release in vivo clinically relevant amounts of the compounds of Formula I. Release occurs both in rodents and primates, with significantly greater plasma levels in primates.

The corresponding data for the compound of Example 28 (rat: acacia/Tween, monkey:propylene glycol) are shown in in Table 5A:

TABLE 5A

| species | time (min) | plasma level of mother compound (μg/ml) | |
|---|---|---|---|
| rat | 30 | 0.033 | 0.046 |
|  | 60 | 0.039 | 0.084 |
|  | 120 | 0.066 | 0.123 |
|  | 240 | 0.039 | 0.034 |
|  | 360 | <0.03 | <003 |
| monkey | 30 | 0.108 | <0.03 |
|  | 90 | 0.159 | 0.098 |
|  | 180 | 0.062 | 0.050 |
|  | 240 | <0.03 | 0.060 |
|  | 540 | 0.036 | 0.070 |

BIOLOGICAL EXAMPLE 8

Antiviral Activity

Compounds of Formula I were tested for HIV-1 activity against wild type $HIV_{IIIB}$ and resistant mutants, with and without the presence of 50% human serum in the XTT-formazan assay where inhibition of cytopathogenic effects is assayed in MT4 cells. In each case the $ED_{50}$ in μM is indicated

TABLE 6

| HIV strain | Example 10 | Example 10 50% serum | Example 11 | Example 11 50% serum |
|---|---|---|---|---|
| wild type | 0.01 | 0.06 | 0.009 | 0.05 |
| L100I | 0.05 | 0.33 | 0.09 | 0.95 |
| K103N | 0.38 | 2.4 | 0.09 | 2.0 |
| Y181C | 0.09 | 0.4 | 0.07 | 3.3 |

The compounds of formula I are thus highly active against various strains of HIV at concentrations achievable in vivo.

BIOLOGICAL EXAMPLE 9

Antiviral Activity

Compounds of the invention have also been compared to the closest prior art compound using a state of the art cell culture assay, wherein human T cell line MT4 cells are grown in RPMI 1640 medium supplemented with 10% fetal calf serum, penicillin and streptomycin seeded into 96 well microplates ($2 \cdot 10^4$ cells/well) infected with 10–20 $TCID_{50}$ per well of $HIV-1_{IIIB}$ (wild type) or mutant virus bearing RT Ile 100, Cys 181 or Asn 103 mutations. Serially diluted test compounds are added to respective wells and the culture incubated at 37° C. in a $CO_2$ enriched atmosphere and the viability of cells is determined at day five or six with XTT vital dye. The results shown below the mean values of a number of determinations. Results are presented as $ED_{50}$ μM.

TABLE 8

| Example | wild type | wild type 50% serum | Ile 100 | Cys 181 | Asn 103 |
|---|---|---|---|---|---|
| Prior art Santa Fe | 0.027 | nd | 0.220 | 0.340 | 0.350 |
| Example 10 | 0.012 | 0.056 | 0.053 | 0.095 | 0.358 |

TABLE 8-continued

| Example | wild type | wild type 50% serum | Ile 100 | Cys 181 | Asn 103 |
|---|---|---|---|---|---|
| Example 11 | 0.008 | 0.058 | 0.100 | 0.069 | 0.080 |
| Example 8 | 0.003 | 0.019 | 0.021 | 0.019 | 0.086 |
| Example 6 | 0.002 | 0.016 | 0.064 | 0.018 | 0.046 |

The compounds of the invention have significantly improved performance against wild type and especially clinically important mutations arising during treatment with NNRTIs.

BIOLOGICAL EXAMPLE 10

Binding Kinetics

The rate of association and dissociation of an NNRTI on the target enzyme can be directly assayed by surface plasmon resonance methodology, wherein reverse transcriptase is immobilized on the surface of a chip and the binding or dissociation of the putative inhibitor is monitored by observing the changes in refractive index caused by the concomitant increase or decrease in chip mass. A compound of the invention (Example 8) was compared to the closest prior art compound from Santa Fe, as depicted above. Experiments were performed on a BIACORE® 2000 (Biacore AB, Uppsala, Sweden), using BIAEVALUATION® software (ver 3.0) for evaluation of data. The binding of the small analyte (NNRTI) to the much larger enzyme results in binding responses in the range of 10–20 RU. The difference in bulk refractive index between running buffer and sample makes it difficult to evaluate data obtained during the injection of sample. During the dissociation phase there is insignificant change in bulk refractive index, thus the binding of the different substances have been evaluated during this phase.

Immobilisation; The enzyme and reference protein were immobilised by direct coupling to primary amines on a CM5 chip (Markgren et al., 1998). Antibody to Fc g (BIACORE® BR-1000-57) was used as reference protein and was immobilised according to instructions if from the manufacturer. HIV reverse transcriptase (Unge et al., 1990) was transferred from 3 M $(NH_4)2SO_4$ to 5 mM Hepes, pH 7.6 containing 4 mM $MgCl_2$, using NANOSEPT® Centrifugal concentrators 10K (Pall Filtron, MA, U.S.A). PT amounts corresponding to 6800–9700 RU were immobilised to the sensor chip. The sensor surface was deactivated by injection of 35 ml of 0.5 M Tris pH 7.6; 4 mM $MgCl_2$, 0.5 M KCl. The immobilisation procedure was carried out at 330° C.

Interaction with inhibitors: Stock solutions of inhibitors (1 mg/ml in DMSO) were dissolved in RT running buffer (10 mM Hepes pH 7.6; 4 mM $MgCl_2$; 0.25 mM spermine; 40 mM KCl; 0.5% TRITON® X-100; 3% DMSO; 0.5% fetal calf serum) to a concentration of 10 mM. Binding of substance to the RT was analysed by injection of 200 ml of the diluted substance, the flow rate was 20 ml/min and the temperature 25° C. After each injection of substance the system was washed by injection of 120 ml of 10% DMSO in RT running buffer.

Figure 3:
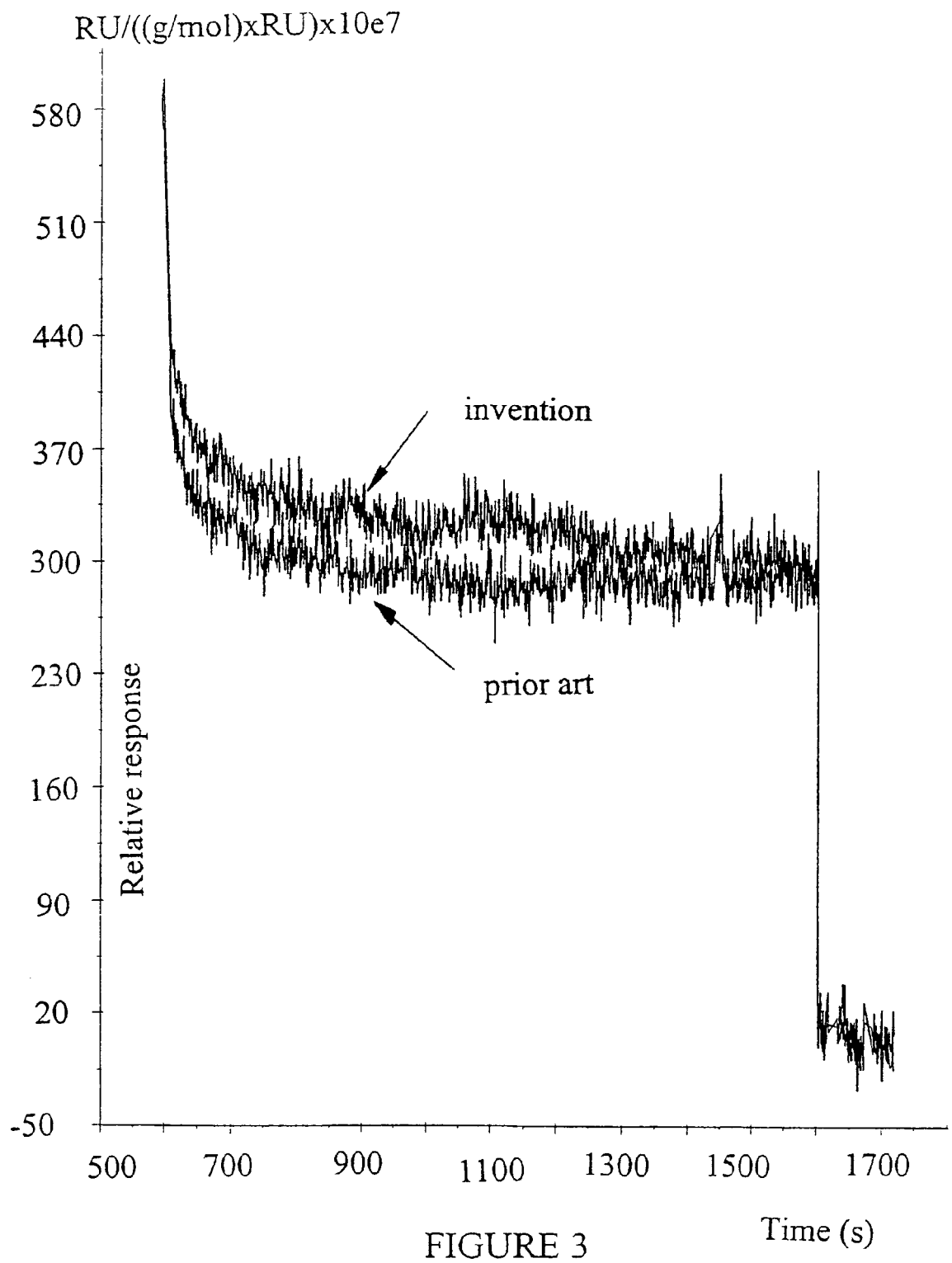
FIG. 3 depicts binding kinetics to reverse transcriptase of a compound of the invention in comparison to a prior art compound, as assayed with surface plasmon resonance methodology as described in Biological Example 10.

The results are depicted in FIG. 3. It is apparent that the compound of the invention and the prior art compound show different interaction kinetics with the compound of the invention dissociating with the lowest rate, indicating a more efficient binding to the enzyme.

REFERENCES

Unge T, Ahola H, Bhikhabhai R, Backbro K, Lovgren S, Fenyo E M, Honigman A, Panet A, Gronowitz J S, Strandberg B, Expression, purification, and crystallization of the HIV-1 reverse, transcriptase (RT). AIDS Res Hum Retroviruses 1990 Nov;6(11):1297–303

Markgren P-O, Hamalainen M, Danielson U H, Screening of compounds interacting with HIV-1 proteinase using optical biosensor technology. Analytical Biochemistry 1998, vol 265, in press.

Although various aspects and embodiments of the invention have been illustrated with reference to the above concrete examples, comparative examples and Figures, it will be appreciated that the invention is in no way limited to these embodiments, but extends throughout the spirit and scope of the attached claims.

The invention claimed is:

1. A pharmaceutical composition comprising the compound denoted (1 S,2S)-N-{cis-2-[6-fluoro, 2-hydroxy, 3-propionylphenyl]-cyclopropyl}-N'-(5-cyanopyrid-2-yl)-urea, or a pharmaceutically acceptable salt thereof; and a pharmaceutically acceptable carrier or diluent therefore, and further comprising one to three additional antiretroviral agents.

2. The composition according to claim 1, wherein said one to three additional antiretroviral agents are selected from the group consisting of AZT, ddI, ddC, D4T, 3TC, adefovir, adefovir dipivoxil, abacavir, bis-POC-PMPA, foscarnet, hydroxyurea, efavirenz, trovirdine, nevirapine, delavirdine, PFA, H2G, ABT 606, ritonavir, saquinavir, indinavir, amprenavir and nelfinavir.

3. A method for the treatment of HIV infection comprising administering to a subject in need thereof an effective amount of a composition according to claim 1.

4. The composition according to claim 2, wherein said additional retroviral agent is bis-POC-PMPA.

5. The composition to claim 2, wherein said additional antiretroviral agent is ritonavir.

6. The composition according to claim 2, wherein said additional retroviral agents are bis-POC-PMPA.

* * * * *